United States Patent
Shtul et al.

(10) Patent No.: US 11,246,479 B2
(45) Date of Patent: Feb. 15, 2022

(54) INTEGRATED ENDOSCOPE CLEANSING SYSTEM

(71) Applicant: Motus GI Medical Technologies Ltd., Tirat HaCarmel (IL)

(72) Inventors: Boris Shtul, Kiryat-Motzkin (IL); Koby Luleko, Eshchar (IL); Mark Pomeranz, Millburn, NJ (US)

(73) Assignee: Motus GI Medical Technologies Ltd., Tirat HaCarmel (IL)

( * ) Notice: Subject to any disclaimer, the term of this patent is extended or adjusted under 35 U.S.C. 154(b) by 0 days.

(21) Appl. No.: 17/267,508

(22) PCT Filed: Aug. 16, 2019

(86) PCT No.: PCT/IL2019/050919
§ 371 (c)(1),
(2) Date: Feb. 10, 2021

(87) PCT Pub. No.: WO2020/035868
PCT Pub. Date: Feb. 20, 2020

(65) Prior Publication Data
US 2021/0244267 A1    Aug. 12, 2021

Related U.S. Application Data

(60) Provisional application No. 62/764,779, filed on Aug. 16, 2018.

(51) Int. Cl.
*A61B 1/00* (2006.01)
*A61B 1/12* (2006.01)
(Continued)

(52) U.S. Cl.
CPC .............. *A61B 1/126* (2013.01); *A61B 1/005* (2013.01); *A61B 1/0052* (2013.01);
(Continued)

(58) Field of Classification Search
None
See application file for complete search history.

(56) References Cited

U.S. PATENT DOCUMENTS 4,270,525 A    6/1981  Furihata
4,526,622 A    7/1985  Takamura et al.
(Continued)

FOREIGN PATENT DOCUMENTS

CN    101065051    10/2007
CN    101301191    11/2008
(Continued)

OTHER PUBLICATIONS

Official Action dated Apr. 26, 2021 From the US Patent and Trademark Office Re. U.S. Appl. No. 16/389,955. (57 Pages).
(Continued)

*Primary Examiner* — Timothy J Neal

(57) ABSTRACT

An integrated endoscope cleansing system (IECS) comprises both an independent cleansing system (ICS) evacuation conduit in communication with an independent cleansing system working station (IWS), and an endoscope insertion tube with a working channel functionally coupled to a vacuum source, under control of an endoscope working station (EWS). In some embodiments, the ICS evacuation conduit is located within the insertion tube, while being functionally coupled to an ICS vacuum source, controlled by the IWS.

23 Claims, 16 Drawing Sheets

(51) Int. Cl.
*A61B 1/005* (2006.01)
*A61B 1/015* (2006.01)
*A61B 1/018* (2006.01)
*A61B 1/05* (2006.01)
*A61B 1/31* (2006.01)

(52) U.S. Cl.
CPC ...... *A61B 1/00114* (2013.01); *A61B 1/00124* (2013.01); *A61B 1/00128* (2013.01); *A61B 1/015* (2013.01); *A61B 1/018* (2013.01); *A61B 1/05* (2013.01); *A61B 1/31* (2013.01)

(56) References Cited

U.S. PATENT DOCUMENTS

| | | |
|---|---|---|
| 5,011,471 A | 4/1991 | Miyazaki et al. |
| 5,096,385 A | 3/1992 | Georgi et al. |
| 5,201,908 A | 4/1993 | Jones |
| 5,279,542 A | 1/1994 | Wilk |
| 5,545,121 A | 8/1996 | Yabe et al. |
| 5,554,098 A | 9/1996 | Yabe et al. |
| 5,630,795 A | 5/1997 | Kuramoto et al. |
| 5,674,182 A | 10/1997 | Suzuki et al. |
| 5,679,110 A | 10/1997 | Hamazaki |
| 5,725,476 A | 3/1998 | Yasui et al. |
| 5,725,477 A | 3/1998 | Yasui et al. |
| 5,788,650 A | 8/1998 | Dotolo |
| 5,924,977 A | 7/1999 | Yabe et al. |
| 6,309,346 B1 | 10/2001 | Farhadi |
| 6,409,657 B1 | 6/2002 | Kawano |
| 6,641,553 B1 | 11/2003 | Chee et al. |
| 6,786,864 B2 | 9/2004 | Matsuura et al. |
| D536,449 S | 2/2007 | Nakajima et al. |
| 2001/0053909 A1 | 12/2001 | Nakada et al. |
| 2004/0127891 A1 | 7/2004 | Humble et al. |
| 2005/0033264 A1 | 2/2005 | Redinger |
| 2005/0085694 A1* | 4/2005 | Nakao .................... A61B 1/012 600/153 |
| 2005/0154262 A1 | 7/2005 | Banik et al. |
| 2005/0256464 A1 | 11/2005 | Pallas |
| 2006/0025729 A1 | 2/2006 | Leiboff et al. |
| 2006/0069304 A1 | 3/2006 | Takemoto et al. |
| 2006/0079861 A1 | 4/2006 | Matasov |
| 2006/0235458 A1 | 10/2006 | Belson |
| 2006/0270906 A1 | 11/2006 | Matsuno |
| 2007/0015965 A1 | 1/2007 | Cox et al. |
| 2007/0234716 A1 | 10/2007 | Hirooka |
| 2008/0188715 A1 | 8/2008 | Fujimoto |
| 2009/0143722 A1 | 6/2009 | Kim |
| 2009/0198212 A1 | 8/2009 | Timberlake et al. |
| 2009/0292172 A1 | 11/2009 | Roskopf et al. |
| 2010/0025644 A1 | 2/2010 | Jockisch |
| 2010/0063358 A1 | 3/2010 | Kessler |
| 2010/0076420 A1 | 3/2010 | Carter |
| 2010/0185056 A1 | 7/2010 | Gordon et al. |
| 2010/0185150 A1 | 7/2010 | Zacharias |
| 2010/0256447 A1 | 10/2010 | Dubi et al. |
| 2010/0298773 A1 | 11/2010 | Nitsan et al. |
| 2011/0034865 A1 | 2/2011 | Wallace |
| 2011/0092892 A1 | 4/2011 | Nitsan et al. |
| 2011/0105845 A1 | 5/2011 | Gordon et al. |
| 2012/0101336 A1 | 4/2012 | Hirsch et al. |
| 2012/0289910 A1 | 11/2012 | Shtul et al. |
| 2013/0046138 A1 | 2/2013 | McLawhorn |
| 2013/0085442 A1 | 4/2013 | Shtul et al. |
| 2013/0131453 A1 | 5/2013 | Imai |
| 2013/0296771 A1 | 11/2013 | Shtul et al. |
| 2013/0303852 A1* | 11/2013 | Hiraga ............... A61B 1/00068 600/118 |
| 2013/0331855 A1 | 12/2013 | Smith et al. |
| 2015/0257633 A1 | 9/2015 | Hassidov et al. |
| 2016/0206805 A1* | 7/2016 | Hassidov .............. A61M 1/74 |
| 2016/0317000 A1* | 11/2016 | Hassidov ........... A61B 1/00006 |
| 2016/0324412 A1 | 11/2016 | Hassidov et al. |
| 2017/0087284 A1* | 3/2017 | Shtul .................. A61B 1/00087 |
| 2017/0173256 A1 | 6/2017 | Hassidov et al. |
| 2018/0020905 A1 | 1/2018 | Chouinard et al. |
| 2018/0235448 A1 | 8/2018 | Hassidov et al. |
| 2019/0247566 A1 | 8/2019 | Hassidov et al. |
| 2019/0298910 A1 | 10/2019 | Hassidov et al. |
| 2021/0076906 A1 | 3/2021 | Hassidov et al. |

FOREIGN PATENT DOCUMENTS

| | | |
|---|---|---|
| CN | 102046064 | 5/2011 |
| CN | 102076271 | 5/2011 |
| CN | 102083356 | 6/2011 |
| CN | 102137615 | 7/2011 |
| CN | 102711590 | 10/2012 |
| CN | 102892445 | 1/2013 |
| DE | 3624428 | 1/1988 |
| EP | 1284120 | 2/2003 |
| EP | 1508294 | 2/2005 |
| EP | 2417896 | 2/2012 |
| JP | 50-81088 | 11/1973 |
| JP | 59-183202 | 12/1984 |
| JP | 05-161711 | 6/1993 |
| JP | 06-011741 | 2/1994 |
| JP | 06-237887 | 8/1994 |
| JP | 06-066605 | 9/1994 |
| JP | 07-136103 | 5/1995 |
| JP | 07-155283 | 6/1995 |
| JP | 07-178040 | 7/1995 |
| JP | 11-216104 | 8/1999 |
| JP | 11-335405 | 12/1999 |
| JP | 2000-014767 | 1/2000 |
| JP | 2001-061760 | 3/2001 |
| JP | 2003-265595 | 9/2003 |
| JP | 2004-008822 | 1/2004 |
| JP | 2004-129951 | 4/2004 |
| JP | 2004-357846 | 12/2004 |
| JP | 2005-095582 | 4/2005 |
| JP | 2005-137423 | 6/2005 |
| JP | 2006-325816 | 12/2006 |
| JP | 2007-278191 | 10/2007 |
| JP | 2007-536073 | 12/2007 |
| JP | 2008-532727 | 8/2008 |
| JP | 2008-206559 | 9/2008 |
| JP | 2011-083329 | 4/2011 |
| JP | 2011-518584 | 6/2011 |
| JP | 2011-520567 | 7/2011 |
| JP | 2013-516300 | 5/2013 |
| JP | 2013-532023 | 8/2013 |
| JP | 2014-018563 | 2/2014 |
| JP | WO 2012/141261 | 7/2014 |
| WO | WO 92/17219 | 10/1992 |
| WO | WO 99/60934 | 12/1999 |
| WO | WO 00/54653 | 9/2000 |
| WO | WO 01/12102 | 2/2001 |
| WO | WO 2005/110580 | 11/2005 |
| WO | WO 2005/117685 | 12/2005 |
| WO | WO 2006/039511 | 4/2006 |
| WO | WO 2006/101908 | 9/2006 |
| WO | WO 2008/093288 | 8/2008 |
| WO | WO 2008/155776 | 12/2008 |
| WO | WO 2009/040744 | 4/2009 |
| WO | WO 2009/095915 | 8/2009 |
| WO | WO 2009/125387 | 10/2009 |
| WO | WO 2009/143201 | 11/2009 |
| WO | WO 2010/138521 | 12/2010 |
| WO | WO 2011/083450 | 7/2011 |
| WO | WO 2011/083451 | 7/2011 |
| WO | WO 2011/158232 | 12/2011 |
| WO | WO 2015/029039 | 3/2015 |
| WO | WO 2015/075721 | 5/2015 |
| WO | WO 2015/155776 | 10/2015 |
| WO | WO 2015/193896 | 12/2015 |

(56) References Cited

FOREIGN PATENT DOCUMENTS

| WO | WO 2016/189533 | 12/2016 |
|---|---|---|
| WO | WO 2020/035868 | 2/2020 |

OTHER PUBLICATIONS

Notice of Reasons for Rejection dated Mar. 2, 2021 From the Japan Patent Office Re. Application No. 2020-016683 and Its Translation Into English. (9 Pages).
International Preliminary Report on Patentability dated Feb. 25, 2021 From the International Bureau of WIPO Re. Application No. PCT/IL2019/050919. (6 Pages).
Applicant-Initiated Interview Summary dated Aug. 4, 2017 From the US Patent and Trademark Office Re. U.S. Appl. No. 14/722,400. (3 Pages).
Applicant-Initiated Interview Summary dated Apr. 10, 2019 From the US Patent and Trademark Office Re. U.S. Appl. No. 15/959,397. (3 pages).
Applicant-Initiated Interview Summary dated Sep. 14, 2017 From the US Patent and Trademark Office Re. U.S. Appl. No. 15/108,601. (3 pages).
Communication Pursuant to Article 94(3) EPC dated Jan. 3, 2017 From the European Patent Office Re. Application No. 15735746.8. (4 Pages).
Communication Pursuant to Article 94(3) EPC dated Apr. 4, 2018 From the European Patent Office Re. Application No. 14816424.7. (5 Pages).
Communication Pursuant to Article 94(3) EPC dated Jun. 5, 2020 From the European Patent Office Re. Application No. 17196947.0. (5 Pages).
Communication Pursuant to Article 94(3) EPC dated May 8, 2020 From the European Patent Office Re. Application No. 14816424.7. (4 Pages).
Communication Pursuant to Article 94(3) EPC dated Nov. 11, 2019 From the European Patent Office Re. Application No. 14771962.9. (5 Pages).
Communication Relating to the Results of the Partial International Search dated Feb. 24, 2015 From the International Searching Authority Re. Application No. PCT/IL2014/051014.
Decision of Refusal dated Sep. 1, 2020 From the Japan Patent Office Re. Application No. 2016-537600 and Its Translation Into English. (10 Pages).
Decision to Grant dated Jan. 6, 2020 From the Japan Patent Office Re. Application No. 2016-559518. (3 Pages).
Decision to Grant Patent dated Jul. 16, 2019 From the Japan Patent Office Re. Application No. 2017-227752 and Its Translation Into English. (6 Pages).
European Search Report and the European Search Opinion dated Mar. 23, 2018 From the European Patent Office Re. Application No. 17196947.0. (7 Pages).
International Preliminary Report on Patentability dated Jun. 2, 2016 From the International Bureau of WIPO Re. Application No. PCT/IL2014/051014.
International Preliminary Report on Patentability dated Dec. 7, 2017 From the International Bureau of WIPO Re. Application No. PCT/IL2016/050544. (8 Pages).
International Preliminary Report on Patentability dated Mar. 10, 2016 From the International Bureau of WIPO Re. Application No. PCT/IL2014/050778.
International Preliminary Report on Patentability dated Oct. 20, 2016 From the International Bureau of WIPO Re. Application No. PCT/IL2015/050379. (9 Pages).
International Preliminary Report on Patentability dated Dec. 29, 2016 From the International Bureau of WIPO Re. Application No. PCT/IL2015/050615. (8 Pages).
International Search Report and the Written Opinion dated May 6, 2015 From the International Searching Authority Re. Application No. PCT/IL2014/051014.

International Search Report and the Written Opinion dated Dec. 8, 2014 From the International Searching Authority Re. Application No. PCT/IL2014/050778.
International Search Report and the Written Opinion dated Sep. 11, 2016 From the International Searching Authority Re. Application No. PCT/IL2016/050544.
International Search Report and the Written Opinion dated Oct. 13, 2015 From the International Searching Authority Re. Application No. PCT/IL2015/050615.
International Search Report and the Written Opinion dated Feb. 16, 2016 From the International Searching Authority Re. Application No. PCT/IL2015/050379.
International Search Report and the Written Opinion dated Oct. 16, 2015 From the International Searching Authority Re. Application No. PCT/IL2015/050379.
International Search Report and the Written Opinion dated Dec. 26, 2019 From the International Searching Authority Re. Application No. PCT/IL2019/050919. (12 Pages).
Invitation to Pay Additional Fees dated Aug. 12, 2015 From the International Searching Authority Re. Application No. PCT/IL2015/050379.
Notice Of Allowance dated Feb. 1, 2019 From the US Patent and Trademark Office Re. U.S. Appl. No. 15/301,968. (18 pages).
Notice Of Allowance dated Dec. 5, 2018 From the US Patent and Trademark Office Re. U.S. Appl. No. 14/915,266. (18 pages).
Notice of Allowance dated Oct. 1, 2020 from the US Patent and Trademark Office Re. U.S. Appl. No. 14/722,400. (26 pages).
Notice of Allowance dated Nov. 13, 2020 from the US Patent and Trademark Office Re. U.S. Appl. No. 15/959,397. (15 pages).
Notice Of Allowance dated Feb. 23, 2018 From the US Patent and Trademark Office Re. U.S. Appl. No. 15/108,601. (8 pages).
Notice of Grounds of Rejection dated Sep. 5, 2018 From the Japan Patent Office Re. Application No. 2016-528831. (6 Pages).
Notice of Grounds of Rejection dated Nov. 6, 2018 From the Japan Patent Office Re. Application No. 2017-227752. (2 Pages).
Notice of Grounds of Rejection dated Jun. 27, 2017 From the Japan Patent Office Re. Application No. 2016-553662. (3 Pages).
Notice of Grounds of Rejection dated Jan. 31, 2017 From the Japan Patent Office Re. Application No. 2016-553662. (3 Pages).
Notice of Reasons for Rejection dated Feb. 6, 2019 From the Japan Patent Office Re. Application No. 2016-559518 and Its Translation Into English. (12 Pages).
Notice of Reasons for Rejection dated Jul. 10, 2018 From the Japan Patent Office Re. Application No. 2016-537600 and Its Summary in English. (9 Pages).
Notice of Reasons for Rejection dated Jun. 16, 2020 From the Japan Patent Office Re. Application No. 2017-559659 and Its Translation Into English. (9 Pages).
Notification of Office Action and Search Report dated Apr. 1, 2019 From the State Intellectual Property Office of the People's Republic of China Re. Application No. 201680002365.5 and Its Summary in English. (9 Pages).
Notification of Office Action and Search Report dated Jun. 3, 2020 From the State Intellectual Property Office of the People's Republic of China Re. Application No. 201680002365.5 and Its Summary in English. (7 Pages).
Notification of Office Action and Search Report dated Apr. 16, 2020 From the State Intellectual Property Office of the People's Republic of China Re. Application No. 201810576718.3 and Its Translation of Office Action Into English. (14 Pages).
Notification of Office Action and Search Report dated Nov. 16, 2017 From the State Intellectual Property Office of the People's Republic of China Re. Application No. 201580037467.6. (9 Pages).
Notification of Office Action and Search Report dated Sep. 23, 2020 From the State Intellectual Property Office of the People's Republic of China Re. Application No. 201810576718.3 and Its Translation of Office Action Into English. (8 Pages).
Notification of Office Action dated Dec. 16, 2019 From the State Intellectual Property Office of the People's Republic of China Re. Application No. 201680002365.5. (4 Pages).
Notification of Reason for Refusal dated May 19, 2020 From the Japan Patent Office Re. Application No. 2016-537600 and Its Translation Into English. (10 Pages).

(56) References Cited

OTHER PUBLICATIONS

Notification of Reasons for Refusal dated Jun. 25, 2019 From the Japan Patent Office Re. Application No. 2016-537600 and Its Summary in English. (8 Pages).
Official Action dated Feb. 1, 2019 From the US Patent and Trademark Office Re. U.S. Appl. No. 15/959,397. (31 pages).
Official Action dated Oct. 2, 2019 From the US Patent and Trademark Office Re. U.S. Appl. No. 14/722,400. (28 pages).
Official Action dated Apr. 5, 2018 From the US Patent and Trademark Office Re. U.S. Appl. No. 14/915,266. (62 pages).
Official Action dated Apr. 6, 2018 From the US Patent and Trademark Office Re. U.S. Appl. No. 15/301,968. (52 pages).
Official Action dated Jun. 6, 2017 from the US Patent and Trademark Office Re. U.S. Appl. No. 14/722,400. (51 pages).
Official Action dated Nov. 8, 2017 From the US Patent and Trademark Office Re. U.S. Appl. No. 14/722,400. (23 pages).
Official Action dated Jul. 1, 2020 from the US Patent and Trademark Office Re. U.S. Appl. No. 15/959,397. (37 pages).
Official Action dated Mar. 15, 2019 From the US Patent and Trademark Office Re. U.S. Appl. No. 14/722,400. (41 pages).
Official Action dated Oct. 19, 2017 From the US Patent and Trademark Office Re. U.S. Appl. No. 15/108,601. (38 pages).
Official Action dated Jul. 31, 2019 From the US Patent and Trademark Office Re. U.S. Appl. No. 15/959,397. (25 pages).
Official Action dated May 31, 2017 From the US Patent and Trademark Office Re. U.S. Appl. No. 15/108,601. (46 Pages).
Restriction Official Action dated Oct. 4, 2018 From the US Patent and Trademark Office Re. U.S. Appl. No. 15/959,397. (10 pages).
Restriction Official Action dated Jan. 16, 2018 From the US Patent and Trademark Office Re. U.S. Appl. No. 14/915,266. (8 pages).
Restriction Official Action dated Nov. 16, 2016 From the US Patent and Trademark Office Re. U.S. Appl. No. 14/722,400. (11 pages).
Restriction Official Action dated Feb. 28, 2017 From the US Patent and Trademark Office Re. U.S. Appl. No. 14/722,400. (11 pages.
Restriction Official Action dated Mar. 29, 2017 From the US Patent and Trademark Office Re. U.S. Appl. No. 15/108,601. (10 Pages).
Supplementary European Search Report and the European Search Opinion dated Dec. 1, 2017 From the European Patent Office Re. Application No. 15776016.6. (10 Pages).
Supplementary European Search Report and the European Search Opinion dated Mar. 21, 2019 From the European Patent Office Re. Application No. 16799477.1. (10 Pages).
Translation Dated Apr. 9, 2019 of Notification of Office Action dated Apr. 1, 2019 From the State Intellectual Property Office of the People's Republic of China Re. Application No. 201680002365.5. (5 Pages).
Translation Dated Jun. 9, 2020 of Notification of Office Action dated Jun. 3, 2020 From the State Intellectual Property Office of the People's Republic of China Re. Application No. 201680002365.5. (2 Pages).
Translation Dated Nov. 14, 2018 of Notice of Grounds of Rejection dated Nov. 6, 2018 From the Japan Patent Office Re. Application No. 2017-227752. (2 Pages).
Translation Dated Jul. 18, 2019 of Notification of Reasons for Refusal dated Jun. 25, 2019 From the Japan Patent Office Re. Application No. 2016-537600. (7 Pages).
Translation Dated Sep. 20, 2018 of Notice of Grounds of Rejection dated Sep. 5, 2018 From the Japan Patent Office Re. Application No. 2016-528831. (7 Pages).
Translation Dated Jul. 24, 2018 of Notice of Reasons for Rejection dated Jul. 10, 2018 From the Japan Patent Office Re. Application No. 2016-537600 and Its Summary in English. (9 Pages).
Translation Dated Dec. 30, 2019 of Notification of Office Action dated Dec. 16, 2019 From the State Intellectual Property Office of the People's Republic of China Re. Application No. 201680002365. 5. (2 Pages).
Translation of Notice of Grounds of Rejection dated Jun. 27, 2017 From the Japan Patent Office Re. Application No. 2016-553662. (3 Pages).
Translation of Notice of Grounds of Rejection dated Jan. 31, 2017 From the Japan Patent Office Re. Application No. 2016-553662. (4 Pages).
Translation of Notification of Office Action dated Nov. 16, 2017 From the State Intellectual Property Office of the People's Republic of China Re. Application No. 201580037467.6. (2 Pages).
Ambrose et al. "Physiological Consequences of Orthograde Lavage Bowel Preparation For Elective Colorectal Surgery: A Review", Journal of the Royal Society of Medicine,76(9): 767-771, Sep. 1983. p. 768, 2nd Paragraph.
Notice of Allowance dated Jul. 21, 2021from the US Patent and Trademark Office Re. U.S. Appl. No. 16/389,955. (13 pages).
Notification of Office Action and Search Report dated Jul. 8, 2021 From the State Intellectual Property Office of the People's Republic of China Re. Application No. 201980067734.2 and Its Translation of Office Action Into English. (6 Pages).
Communication Pursuant to Article 94(3) EPC dated Apr. 30, 2021 From the European Patent Office Re. Application No. 16799477.1. (10 Pages).
Notice of Reason(s) for Rejection dated Aug. 10, 2021 From the Japan Patent Office Re. Application No. 2016-537600. (1 Page).
Notice of Reason(s) for Rejection dated Aug. 17, 2021 From the Japan Patent Office Re. Application No. 2016-537600. ( 1 Page).
Communication Pursuant to Article 94(3) EPC dated Sep. 22, 2021 From the European Patent Office Re. Application No. 19850154.6. (6 Pages).

\* cited by examiner

INTEGRATED ENDOSCOPE CLEANSING SYSTEM

RELATED APPLICATIONS

This application is a National Phase of PCT Patent Application No. PCT/IL2019/050919 having International filing date of Aug. 16, 2019, which claims the benefit of priority under 35 USC § 119(e) of U.S. Provisional Patent Application No. 62/764,779 filed on Aug. 16, 2018. The contents of the above applications are all incorporated by reference as if fully set forth herein in their entirety.

FIELD AND BACKGROUND OF THE INVENTION

The present invention, in some embodiments thereof, relates to a body organ lumen cleaning system, and, more particularly, but not exclusively, to an integrated endoscope body organ lumen cleansing system (IECS).

While partially homogenizing food's original structure, gastrointestinal processing also adds new structure; for example, by aggregating digested particles, and by controlling stool water content. As captured by the Bristol Stool Scale, for example, stool is classified of a scale from 7 (completely liquid) to 1 (small hard lumps). Variables affecting the state of fecal aggregation and fluid content, as well as completeness of food digestion, include the frequency of defecation (normally ranging from five times a day to twice a week), and the speed at which food passes through the gastrointestinal tract (10 hours to 4 days is normal). Gut flora and secretions of the digestive tract also become part of the stool.

A colonoscope provides means for optically and/or electronically imaging the colon and its contents, for example, to look for cancerous and/or pre-cancerous polyps. For effective viewing, a common practice before colonoscopy is to clear as much of a colon's contents as possible, sometimes by aggressive changes to diet and/or by administration of purgatives. In some methods of colon observation, imaging occurs while flushing or washing a portion of the colon with an irrigating fluid. Irrigating fluid, fecal matter and/or other colon contents are drawn out of the colon by suction and/or other methods for transporting matter out of the body. The following patent applications relate to the field of endeavor of the current application: U.S. Patent Application 2010/0185056 by Tal Gordon et al.; U.S. Patent Application 2011/0105845 by Tal Gordon et al.; and U.S. Patent Application 2012/0101336 by Yoav Hirsch et al.

SUMMARY OF THE INVENTION

There is provided, in accordance with some embodiments of the present disclosure, an integrated endoscope cleansing system (IECS) comprising: an endoscope having: at least one insertion tube in communication with an endoscope working station (EWS), and at least one working channel functionally coupled to at least one endoscope cleaning system (ECS) vacuum source, wherein the EWS is configured to control the ECS vacuum source; and an independent cleansing system (ICS) having: an independent cleansing system working station (IWS), and having at least one ICS evacuation conduit located within at least the insertion tube and functionally coupled to an ICS vacuum source; wherein the IWS is configured to control the ICS vacuum source.

In some embodiments, the evacuation conduit and the working channel together comprise a single channel within the insert tube.

In some embodiments, the evacuation conduit and the working channel together comprise a single tube within the insert tube to which both the ICS vacuum source and the ECS vacuum source are functionally coupled.

In some embodiments, the IECS comprises at least one mode of operation consisting of at least one of: (a) ICS/ECS Master/Slave mode of operation; (b) ICS/ECS "Smart" Master/Slave mode of operation; and (c) ECS/ICS Master/Slave mode of operation.

In some embodiments, the IECS comprises at least one mode of operation toggle switch configured to toggle between at least two of the modes of operation.

In some embodiments, the IECS is configured for manual activation of at least one of the ECS and ICS.

In some embodiments, the IECS, in the manual mode of operation, is configured to manually activate each of the ECS and ICS individually, sequentially or concurrently.

In some embodiments, in the ICS/ECS Master/Slave mode of operation, the ICS is activated and configured to automatically activate the ECS.

In some embodiments, at least one of the IWS and EWS comprises at least processor and at least one sensor configured to communicate at least one operating parameter to the processor.

In some embodiments, the at least one operating parameter comprises at least one of lumen pressure and flow of matter in a lumen of at least one of the working channel and evacuation conduit.

In some embodiments, in the ICS/ECS "Smart" Master/Slave mode of operation, the IWS processor is configured to receive and process the at least one operating parameter received from the EWS processor and automatically activate the ECS based on the received parameters.

In some embodiments, in the ECS/ICS Master/Slave mode of operation, the EWS processor is configured to receive and process the at least one operating parameter from the sensor and to automatically activate the ICS based on the received parameter.

In some embodiments, the endoscope comprises a colonoscope.

In some embodiments, the insertion tube is configured to receive IECS components associated with at least one operating function group.

In some embodiments, the at least one operating function group comprises at least one of: (a) an endoscope operating function group; (b) an ECS operating function group; and (c) an ICS operating function group.

In some embodiments, the endoscope operating function group comprises at least one of an endoscope angulation control navigation cable, light wiring and circuitry, power circuitry, image acquisition camera and circuitry and sensors and associated circuitry.

In some embodiments, the ECS operating function group comprises at least one suction/working channel and at least one irrigation and/or air/water supply tube.

In some embodiments, the ICS operating function group comprises at least one irrigation and/or air/water supply tube and at least one evacuation conduit.

In some embodiments, the IECS comprises an interface.

In some embodiments, the interface is configured to couple an umbilical cable originating from the IWS to the insertion tube.

In some embodiments, the umbilical cable comprises at least one irrigation tube and at least one evacuation conduit.

In some embodiments, the umbilical cable comprises sensor circuitry.

In some embodiments, the umbilical cable is disposable.

In some embodiments, the insertion tube comprises at least one bendable portion.

In some embodiments, the bendable portion comprises a resilient, braided and/or ribbed wall.

In some embodiments, tubes housed within the bendable portion are bendable in accordance with the bending of the bendable portion.

In some embodiments, the insertion tube comprises a distal tip having at least one opening.

In some embodiments, the at least one opening comprises at least one fluid jet nozzle.

There is provided, in accordance with some embodiments of the present disclosure, a method for a colonoscopy procedure, comprising providing an integrated endoscope cleansing system (IECS) comprising: an endoscope having: at least one mode of operation toggle switch and at least one insertion tube in communication with an endoscope working station (EWS), and at least one working channel functionally coupled to at least one endoscope cleaning system (ECS) vacuum source, wherein the EWS configured to control the ECS vacuum source; and an independent cleansing system (ICS) having: an independent cleansing system working station (IWS), and at least one ICS evacuation conduit located within at least the insertion tube and functionally coupled to an ICS vacuum source, wherein the IWS configured to control the ICS vacuum source; introducing the IECS insertion tube into a colon; and performing the colonoscopy procedure; wherein performing the colonoscopy procedure comprises adjusting the mode of operation toggle switch between a first and a second mode of operation during the colonoscopy procedure, and wherein the first and second modes differ in configuration of a source of control of at least one of the ICS and ECS vacuum sources.

In some embodiments, the first and second modes of operations are selected from among the group consisting of: (a) a manual mode of operation; (b) ICS/ECS Master/Slave mode of operation; (c) ICS/ECS "Smart" Master/Slave mode of operation; and (d) ECS/ICS Master/Slave mode of operation.

In some embodiments, in the manual mode of operation the IECS is configured for manual activation of at least one of the ECS and ICS.

In some embodiments, in the ICS/ECS Master/Slave mode of operation the ICS is activated and configured to automatically activate the ECS.

In some embodiments, at least one of the IWS and EWS comprises at least processor and at least one sensor configured to communicate at least one operating parameter to the processor.

In some embodiments, the at least one operating parameter comprises at least one of lumen pressure and flow of matter in a lumen of at least one of the working channel and evacuation conduit.

In some embodiments, in the ICS/ECS "Smart" Master/Slave mode of operation, the IWS processor is configured to receive and process the at least one operating parameter received from the EWS processor and automatically activate the ECS based on the received parameters.

In some embodiments, in the ECS/ICS Master/Slave mode of operation the EWS processor is configured to receive and process the at least one operating parameter from the sensor and to automatically activate the ICS based on the received parameter.

In some embodiments, adjusting the mode of operation toggle switch comprises selecting the ICS/ECS Master/Slave mode of operation.

In some embodiments, the method further comprises: activating the ICS; advancing the IECS through the colon up to a cecum while concurrently cleansing the colon with the ICS; and automatically activating the ECS by the ICS when needed throughout the advancement.

In some embodiments, the IECS comprises at least one image acquisition camera and circuitry and the method further comprising: upon reaching the cecum, adjusting the mode of operation toggle switch and selecting ECS/ICS Master/Slave mode of operation; activating image acquisition camera and circuitry; gradually retracting the IECS from the cecum; activating the ECS when needed; automatically activating ICS by ECS when needed; and removing the IECS from colon.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as monitor fluid input and output, waste matter suction and similar, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

DESCRIPTION OF SPECIFIC EMBODIMENTS OF THE INVENTION

Figure 1:
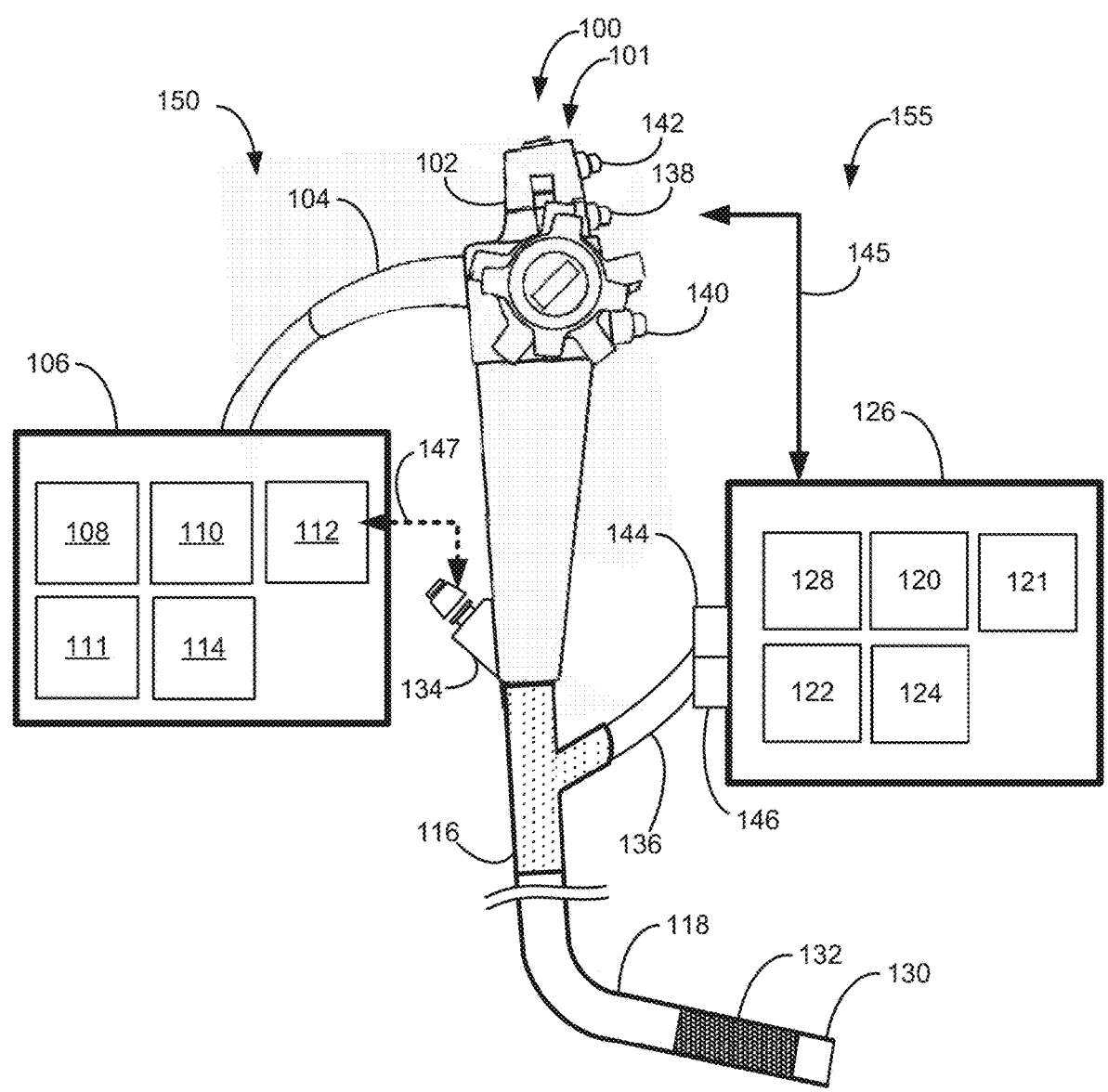
FIG. 1 is a plan view and simplified block diagram illustration of an integrated endoscope and cleaning system (IECS) in accordance with some embodiments of the invention.

The present invention, in some embodiments thereof, relates to a body organ lumen cleaning system, and, more particularly, but not exclusively, to an integrated endoscope body organ lumen cleaning system (IECS).

As used herein, the term "Proximal" means close to a user and/or away from the body being treated. The term "Distal" means away from the user and/or close to the body being treated.

An aspect of some embodiments of the invention relates to an integrated endoscope cleaning system (IECS). In some embodiments, the IECS is configured to operate in one or more modes of operation. In some embodiments, The IECS comprises one or more modes of operation toggle switches configured to toggle the IECS between one or more modes of operations.

Herein, the term "toggle switch" is used (particularly in the phrasing "mode of operation toggle switch") to refer to any switching mechanism, (e.g., mechanical and/or electronic, operating by means of software and/or hardware, and optionally comprising one or a plurality of separately switched selections) which allows selecting from among two, three, four, five, or more modes of operation. For example, in some embodiments, a single switch toggles between two or more modes of operation; in some embodiments, two or more switches are functionally combined as a toggle switch configured to select from among two or more modes of operation.

In some embodiments, the IECS comprises one or more lumen cleaning systems. In some embodiments, the IECS comprises an endoscope cleaning system (ECS). In some embodiments, the IECS comprises an independent cleaning system (ICS). In some embodiments, the IECS comprises at least one an endoscope cleaning system (ECS) and at least one independent cleaning system (ICS). In some embodiments, the endoscope cleaning system (ECS) and the independent cleaning system (ICS) are housed together at least within an endoscope insertion tube.

In some embodiments, one or more modes of operation comprise a manual mode of operation. In some embodiments, in the manual mode of operation the IECS is configured for manual activation to enable a user to activate at least one of the endoscope cleaning system (ECS) and the independent cleaning system (ICS). In some embodiments, the manual mode of operation the IECS is configured to activate both the endoscope cleaning system (ECS) and the independent cleaning system (ICS) concurrently.

In some embodiments, one or more modes of operation comprise an ICS/ECS Master/Slave mode of operation. In some embodiments, the ICS/ECS Master/Slave mode of operation the IECS is configured to activate the independent cleaning system (ICS). In some embodiments, the independent cleaning system (ICS) is configured to automatically activate the endoscope cleaning system (ECS) as needed.

In some embodiments, at least one of the ICS and ECS comprises one or more corresponding Independent system Working Station (IWS) and Endoscope Working Station (EWS). In some embodiments, at least one of the IWS and EWS comprises at least one processor configured to at least one of process imager signals, process sensor signals, control one or more of the pumps and/or valves, and communicate processed information to a monitor.

In some embodiments, one or more modes of operation comprise an ICS/ECS "Smart" Master/Slave mode of operation. In some embodiments, in the ICS/ECS "Smart" Master/Slave mode of operation the IECS is configured to activate the endoscope cleaning system (ECS). In some embodiments, an independent cleaning system (ICS) processor is configured to receive and process operating parameters received from an Endoscope Working Station (EWS) processor and automatically activate the ICS based on the received parameters.

In some embodiments, one or more modes of operation comprises ECS/ICS Master/Slave mode of operation. In some embodiments, the ECS/ICS Master/Slave mode of operation the IECS is configured to activate the endoscope cleaning system (ECS). In some embodiments, the endoscope cleaning system (ECS) EWS processor is configured to receive and process operating parameters and to automatically activate the ICS as needed based on the received parameters.

An aspect of some embodiments of the invention relates to an IECS. In some embodiments the interface couples an umbilical cable originating from the IWS to the IECS insertion tube. In some embodiments, the umbilical cable accommodates at least one ICS evacuation conduit. In some embodiments, the umbilical cable accommodates at least one ICS irrigation tube. In some embodiments, the umbilical cable accommodates at least one sensor circuitry in communication with the IWS processor. In some embodiments, the umbilical cable is disposable.

Optionally, in some embodiments the interface comprises a flexible joint configured to allow flexion and extension of a branch of the interface. In some embodiments, the interface comprises conduits that communicate with corresponding conduits permanently accommodated within the insertion tube.

An aspect of some embodiments of the invention relates to an endoscope insertion tube bendable portion. In some embodiments, the bendable portion is configured to be driven by one or more endoscope navigation cables. In some embodiments, the bendable portion is configured to bend radially at least up to 180 degrees in vertical (up and down) directions and at least up to 160 degrees in horizontal (left and right) directions.

An aspect of some embodiments of the invention relates to an IECS insertion tube distal tip comprises one or more openings. In some embodiments, a first end of one or more conduits opens to one or more openings at the tip of the insertion tube. In some embodiments, a second end of the one or more conduits opens to one or more ports in the tube. In some embodiments, the ports are located between the colonoscope handle end and the one or more openings at the tip of the insertion tube. In some embodiments, the one or more of the conduits are permanently accommodated within the tube. In some embodiments, the one or more openings comprise fluid jet nozzles that eject fluid jets. In some embodiments, one or more fluid/air apertures are angled to aim fluid/air at a lens of a camera received inside the distal tip.

Reference is now made to FIG. 1, which is a plan view and simplified block diagram illustration of an integrated endoscope and cleaning system (IECS) in accordance with some embodiments of the invention. As shown in the exemplary embodiment depicted in FIG. 1, an IECS 100 comprises an endoscope 101 having an endoscope handle 102, an interface portion 116 and endoscope insertion tube 118 including a distal end tip 130 and a bendable portion 132. In some embodiments, endoscope 101 comprises a colonoscope. In some embodiments, IECS 100 comprises one or more lumen cleaning systems: an endoscope cleaning system (ECS) 150 and an independent cleaning system (ICS) 155.

In some embodiments, ECS 150 comprises an endoscope handle 102 in fluid and data communication with an Endoscope Working Station (EWS) 106 via at least one umbilical cable 104 carrying at least one or more air and/or water supply tubes in fluid communication with respective EWS 106 air 108 and/or water 110 sources communicating with respective air 178 and/or water 170 supply tubes and one or more suction tubes in fluid communication with an EWS source of vacuum 112. In some embodiments, EWS 106 comprises a waste reservoir 111. In some embodiments, EWS 106 comprises a processor 114 having a database. In some embodiments, handle 102 is in data communication with an EWS 106 processor 114. Additionally and optionally, EWS 106 processor 124 is configured to receive data from and control one or more fluid pumps, light and power sources (not shown).

In some embodiments, integrated endoscope and cleaning system (IECS) 100 independent cleaning system (ICS) includes at least one ICS Working Station (IWS) 126 in fluid and data communication with endoscope insertion tube body 118 via at least one umbilical cable 136 carrying at least one or more air and/or water supply tubes (not shown) in fluid communication with respective IWS 126 air 128 and/or water 120 sources via one or more control valves 144 and one or more suction tubes in fluid communication with an CSWS source of vacuum 122 and controlled by one or more valves 146. Additionally and optionally, IWS 126 comprises at least one evacuation reservoir 121 and at least one processor 124 having a database and receiving data from and controlling one or more fluid pumps, light, image acquisition and power sources (not shown). In some embodiments, IWS 126 processor 124 is in data communication with handle 102 as indicated in FIG. 1 by an arrow designated reference numeral 145.

In some embodiments and optionally, ICS 155 comprises one or more fluid jet nozzles (not shown) configured eject fluid jets to agitate and break up matter in an examined lumen e.g., fecal matter in the colon. In some embodiments the jet nozzles eject directional fluid jets directed by IWS 126. In some embodiments, the jet nozzles are located adjacent a camera head and are directed to clean a camera lens from debris.

In some embodiments, endoscope handle 102 comprises at least one suction control valve 138 and at least one air/water control valve 140. In some embodiments, suction control valve 138 and air/water control valve 140 are configured to be activated manually by a user. Alternatively and optionally, in some embodiments, suction control valve 138 and air/water control valve 140 are in data communication with IWS 126 processor 114. Optionally, in some embodiments, suction control valve 138 and air/water control valve 140 are controlled by at least one of manually and IWS 126 processor 114. In some embodiments and as explained in greater detail elsewhere herein, endoscope handle 102 comprises at least one IECS mode of operation toggle switch 142. In some embodiments, mode of operation toggle switch 142 is configured to select between one or more modes of operation of IECS 100.

In some embodiments and as explained in greater detail in relation to embodiments elsewhere herein (for example, in relation to FIGS. 2A-2B, 3A, 4A, 5A, and/or 9) endoscope insertion tube 118 comprises at least one working channel 134 optionally functionally coupled to at least one EWS 106 vacuum source 112 as indicated by broken line arrow 147 and at least one fluid supply tube 148 comprising at least one of air 178 and/or water 170 supply tube in fluid communication with at least one of EWS 106 air 108 and/or water 110 sources. In some embodiments, endoscope insertion tube 118 comprises at least one evacuation tube 152 functionally coupled to at least one IWS 126 vacuum source 122 and/or at least one fluid supply tube 154 comprising at least one of air and or water supply tubes in fluid communication with at least one of IWS 126 air 128 and/or water 120 sources.

For purposes of presentation, tube/channel/conduit elements are presented as separate elements in some examples, and in particular are described as being separately assigned to EWS 106 and IWS 126 (e.g., via function groups 204 and 206). However, it should be understood that these elements are optionally shared by being in a fluid interconnection, with control by the EWS 106, IWS 126, or a combination thereof. Control is conferred, shared, and/or transferred, e.g., by the use of control valves 138, 140, 144, 146. In some embodiments, evacuation tube 152 joins to (and optionally comprises) working channel 134, with working channel 134 being joined (e.g., by means of a Y-tube connection) to both the EWS 106 (e.g., via control valve 138) and to the IWS 126 (e.g., via control valve 146). Additionally or alternatively, evacuation tube 152 and working channel 134 together comprise a single channel within the insertion tube, for example as a single tube shared between EWS 106 and IWS 126, or as a plurality of tubes shared between EWS 106 and IWS 126. Some potential advantages of this stem from joint and/or or alternative application of suction to the same channel. For example, in some embodiments, IWS 126 directly provides a high throughput alternative and/or additional mode of operation to the same working channel used for evacuation by EWS 106 (e.g., by application of a higher level of suction). In some embodiments, one of EWS 106 and IWS 126 provides capability for modulation of evacuation pressure, while the other provides a constant or merely on/off source of evacuation pressure. Optionally, the modulation is sensor-driven. For example, upon the sensed occurrence of blockage and/or the beginning of obstruction, one of EWS 106 and IWS 126 operates to clear the block by reversing pressure, while vacuum pressure from the other is optionally switched off, or alternatively left on but modulated by pressure changes driven by the other. Sharing a tube allows the blockage clearance and/or other sensor driven capabilities of one station to assist the evacuation capabilities (perhaps more basic) of the other station. In some embodiments, there are a limited number of conduits available, and it is preferred to concentrate evacuation to, e.g., just one of them, so that another is available as a working channel for a tools. Potentially, one of EWS 106 and IWS 126 is more aggressive in applying suction, and it is preferred to have this aggressive suction active only at selected times—for example, during cleaning under the active guidance of an operator. This potentially increases safety of the device at other times, improves handling, makes control of insufflation level easier, and/or reduces pump noise or other evacuation-related side effects. In some embodiments, the device is configured to switch between using one tube for evacuation and two (that is, switch between using a lesser and greater number of tubes), allowing reconfiguration of evacuation capacity (e.g., in the midst of a procedure) to suit the changing demands of different phases of the procedure.

Additionally or alternatively, in some embodiments, fluid supply tube 154 joins to (and optionally comprises) fluid supply tube 148, with fluid supply tube 148 being joined (e.g., by means of a Y-tube connection) to both the EWS 106 (e.g., via control valve 140) and the IWS 126 (e.g., via control valve 144). Additionally or alternatively, fluid supply tube 154 and fluid supply tube 148 together comprise a single channel within the insertion tube; for example as a single tube shared between EWS 106 and IWS 126, or as a plurality of tubes shared between EWS 106 and IWS 126. As for evacuation, sharing a single tube potentially frees up another tube for other uses in some embodiments. As for evacuation, sharing one or more tubes potentially allows cross-provision of capabilities. For example, IWS 126 may be configured to supply a different fluid or mix of fluids (e.g., an air/liquid mix for producing jets) than EWS 106. In some embodiments, the device is configured to switch between using one tube for fluid supply and two (that is, switch between using a lesser and greater number of tubes), allowing reconfiguration of irrigation capacity (e.g., in the midst of a procedure) to suit the changing demands of different phases of the procedure.

IECS Modes of Operation

As will be explained in greater detail herein IECS 100 is configured to operate in one or more optional modes of operation including at least:
  a) Manual mode of operation
  b) ICS/ECS Master/Slave mode of operation
  c) ICS/ECS "Smart" Master/Slave mode of operation
  d) ECS/ICS Master/Slave mode of operation Manual Mode of Operation Reference is now made to FIG. 2A-B, which are a simplified block diagrams of a mode of operation of IECS 100 in accordance with some embodiments of the invention. As shown in the exemplary embodiments depicted in FIG. 2A-2B and disclosed elsewhere herein, IECS 100 comprises at least three function groups:
  a) An endoscope operating function group 202 controlled by an operator 250 and optionally by EWS 106 and comprising at least one or more endoscope angulation controls and navigation cables, light wiring and circuitry, power circuitry, image acquisition camera and circuitry and sensors and associated circuitry;
  b) An ECS 150 function group 204 controlled by EWS 106 and comprising one or more suction/working channels 134 and one or more irrigation and/or air 178/water 170 supply tubes coupled to air 108 and/or water 110 sources via one or more valves 140. In some embodiments, one or more suction/working channels 134 are functionally coupled to vacuum source 112 via one or more suction control valves 138. In some embodiments, suction/working channels 134 and one or more irrigation and/or air 178/water 170 supply tubes are one or more irrigation and/or air/water supply tubes disposed at least in part through endoscope 101 insertion tube 118. Additionally and optionally, ECS 150 function group 204 comprises sensors and their associated circuitry in communication with EWS 106 processor 114.
  c) An ICS 155 function group 206 controlled by IWS 126 and comprising one or more irrigation and/or air/water supply tubes coupled to air 128 and/or water 120 sources via one or more valves 144 and one or more evacuation conduits 152 in fluid communication with vacuum source 122 via one or more vacuum control valves 146. In some embodiments, one or more evacuation conduits 152 and/or one or more air/water supply tubes 154 are disposed at least in part through endoscope 101 insertion tube 118. Additionally and optionally, ICS 155 function group 206 comprises sensors and their associated circuitry in communication with IWS 126 processor 124.

Figure 2A:
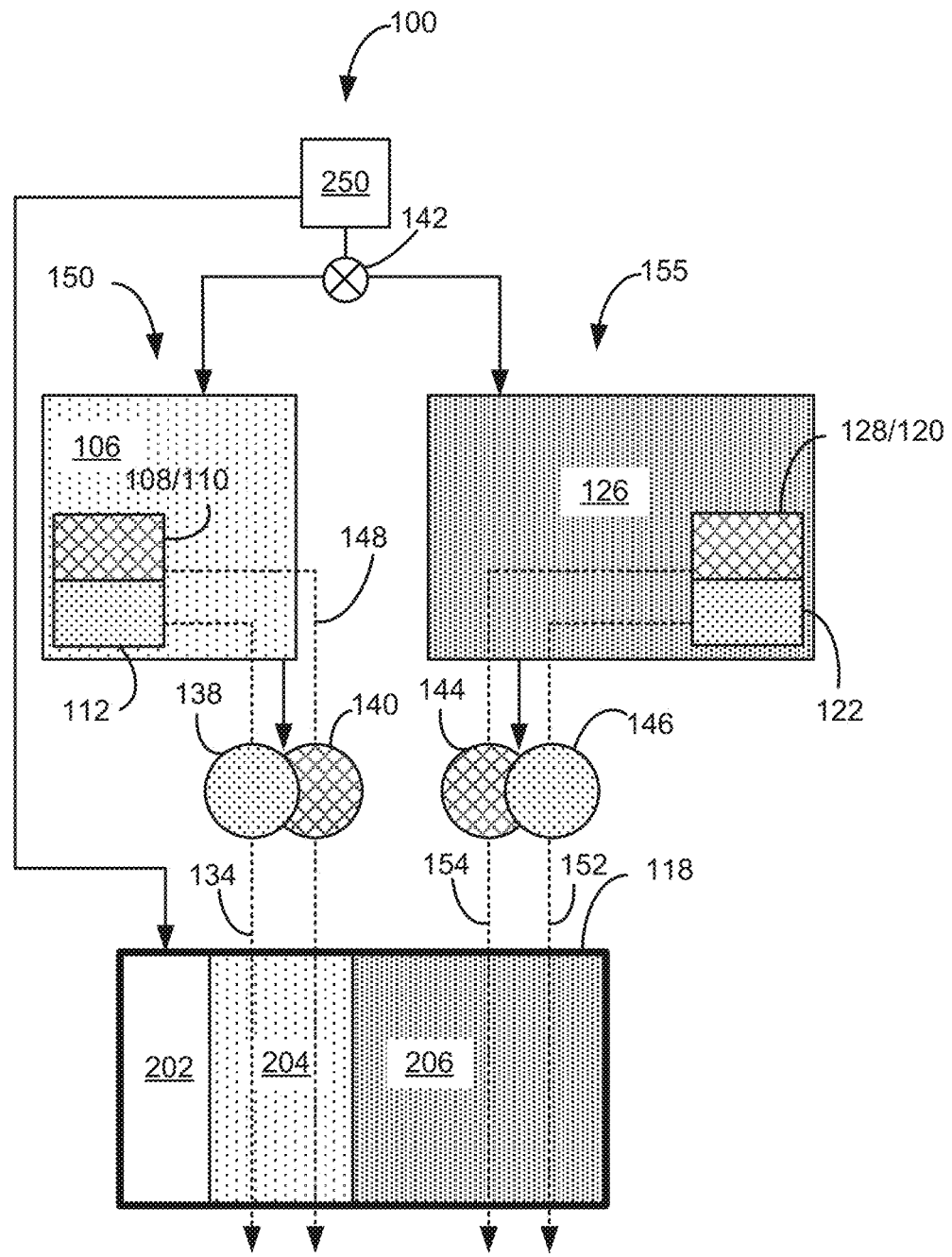
FIGS. 2A-2B are a simplified block diagrams of a mode of operation of IECS in accordance with some embodiments of the invention.
Figure 2B:
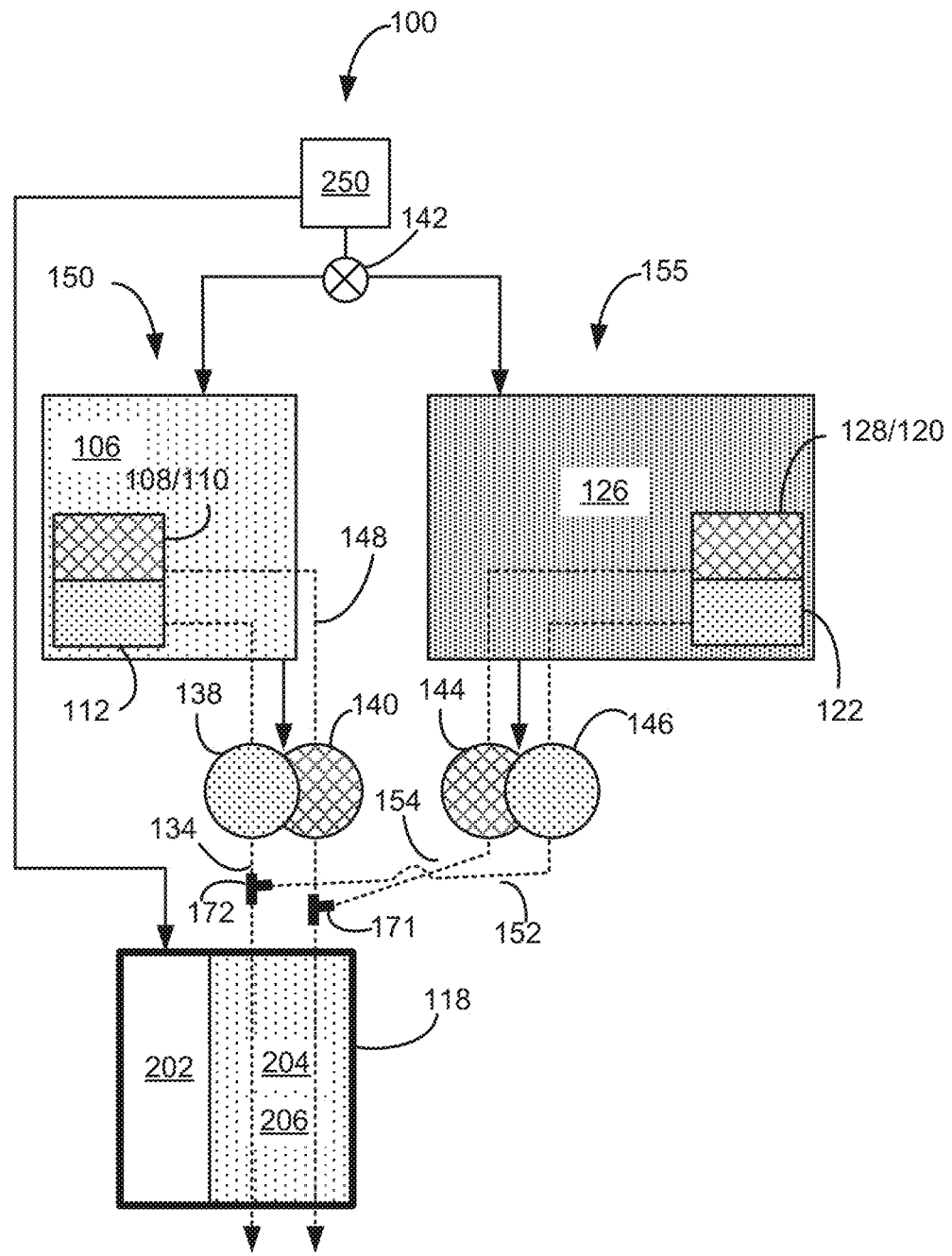

In the exemplary configuration depicted in FIGS. 2A-2B, an operator 250 toggles manually between operation of ECS 150 alone, ICS 155 alone or joint manual activation of ECS 150 and ICS 155. In some embodiments, ICS 155 comprises fluid jet nozzles (not shown) configured to agitate and break up matter in the examined lumen e.g., fecal matter in the colon. The manual mode of operation provides for local imaging and cleaning of a portion of a colon employing ECS 150 when needed and activation of ICS 155 under conditions in which the ability of ECS cleaning operation is insufficient and requires supplementary cleaning and/or agitation and break up of matter in the examined lumen. In some embodiments, one or more directional jet nozzles are located on a camera head and directed by IWS 126.

In some embodiments, ECS function group 204 and/or ICS function group 206 enter endoscope 101 via interface portion 116 and are accommodated within endoscope 101 insertion tube 118 (FIG. 1). In some embodiments, ECS 150 group 204 and optionally endoscope operating group 202 are controlled and supplied from air 108/water 110 and or vacuum 112 sources by EWS 106. In some embodiments, ICS 155 group 206 is independently controlled and supplied from air 128/water 120 and or vacuum 122 sources in IWS 126.

In some embodiments and as shown in FIGS. 2A-2B, IECS 100 comprises one or more mode of operation toggle switches 142. In some embodiments, mode of operation toggle switch 142 is configured to be adjusted manually by an operator 250 or, alternatively and optionally, by an IECS 100 computer (not shown) and set at a desired mode of operation. In some embodiments, mode of operation toggle switch 142 is optionally set to operate ECS 150. EWS 106 is configured to activate and operate at least air 108/water 110 and/or vacuum 112 sources as well as air/water control valve 140 and suction control valve 138 respectively corresponding to the setting of mode of operation toggle switch 142.

In the exemplary configuration shown in FIGS. 2A-2B, air and/or water flow through endoscope supply and/or irrigation tubes 140 disposed in ECS 150 group 204 and vacuum source 112 supplies endoscope working channel 134 with suction. EWS 150 controls one or more suction control valves 138 and one or more air/water supply valves 140.

In some embodiments, mode of operation toggle switch 142 is optionally set to operate ICS 155. IWS 126 is configured to activate and operate at least air 128/water 120 and/or vacuum 122 sources as well as air/water control valve 144 and suction control valve 146 respectively corresponding to the setting mode of operation toggle switch 142.

In the exemplary configuration shown in FIGS. 2A-2B, air and/or water flow through endoscope supply and/or irrigation tubes 154 disposed in ICS 155 group 206 and vacuum source 122 supplies evacuation conduit 152 with suction. CSWS 155 controls one or more suction control valves 146 and one or more air/water supply valves 144.

Distinguishing between FIGS. 2A and 2B, function groups 206 and 204 are shown merged to a single group of tubes. In some embodiments, irrigation tubes 154 and 148 are merged (e.g., at Y-connector 171) and continue as a single tube through insertion tube 118. In some embodiments (additionally or alternatively) evacuation conduit 152 and working channel 134 are merged (e.g., at Y-connector 172) and continue as a single tube through insertion tube 118.

In some embodiments, the merging is four-way; e.g. irrigation tubes 154 and 148 are merged at a four-way connector to connect to both of control valves 140, 144, and/or evacuation conduit 152 and working channel 134 are merged at a four-way connector to connect to both of control valves 138, 146.

Figure 9:
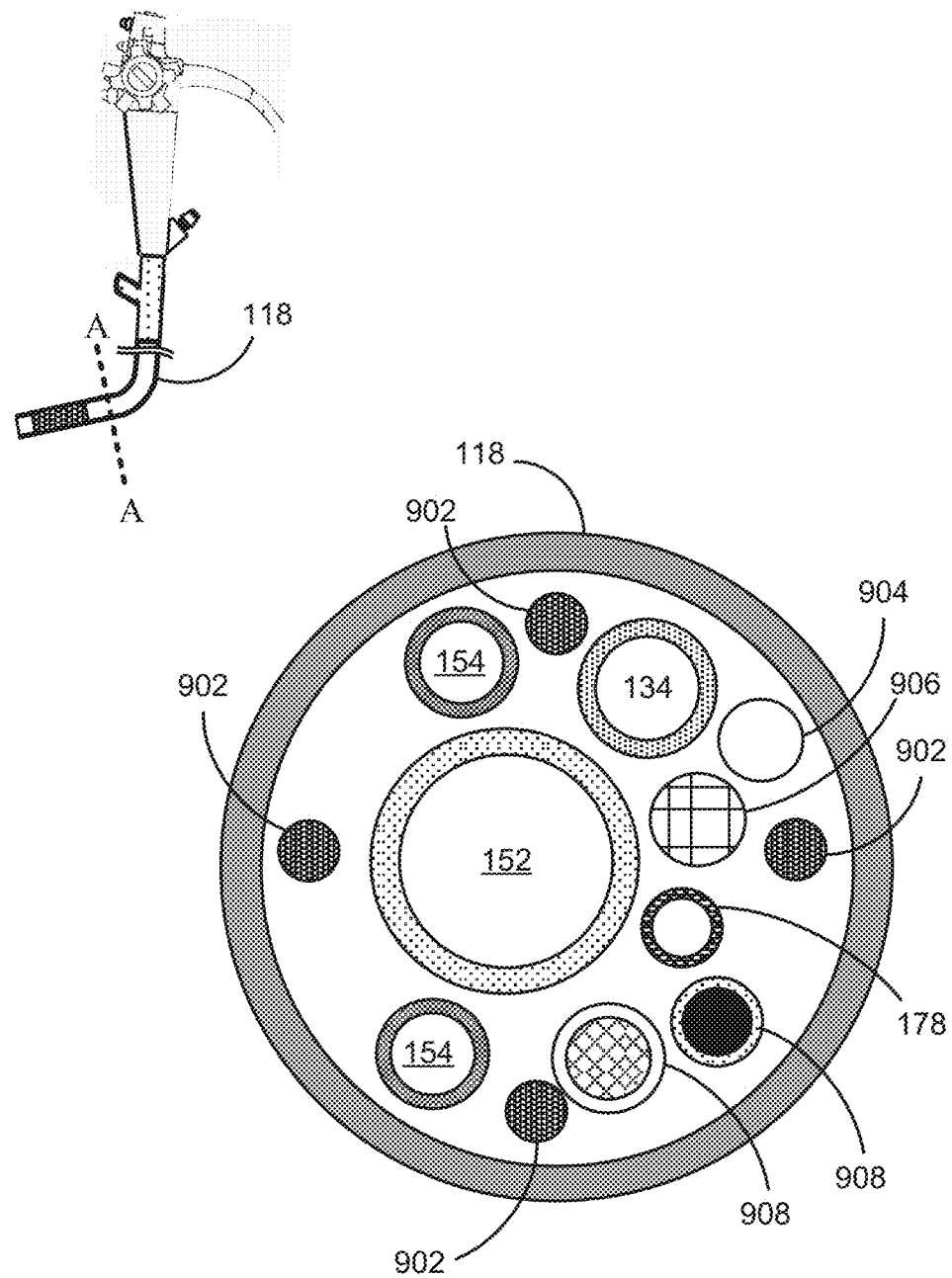
FIG. 9 is a cross-section view simplified illustration of IECS insertion tube in accordance with some embodiments of the invention.

Although drawn separately in other embodiments herein for purposes of presentation, it should be understood that in alternative embodiments of any of these, function group 206 and function group 204 share one or more tubes (e.g., by 3-way and/or 4-way connections) for example as just described in relation to FIG. 2B, and/or as described in relation to FIG. 9 and/or FIG. 1, herein.

ICS/ECS Master/Slave Mode of Operation

Figure 3A:
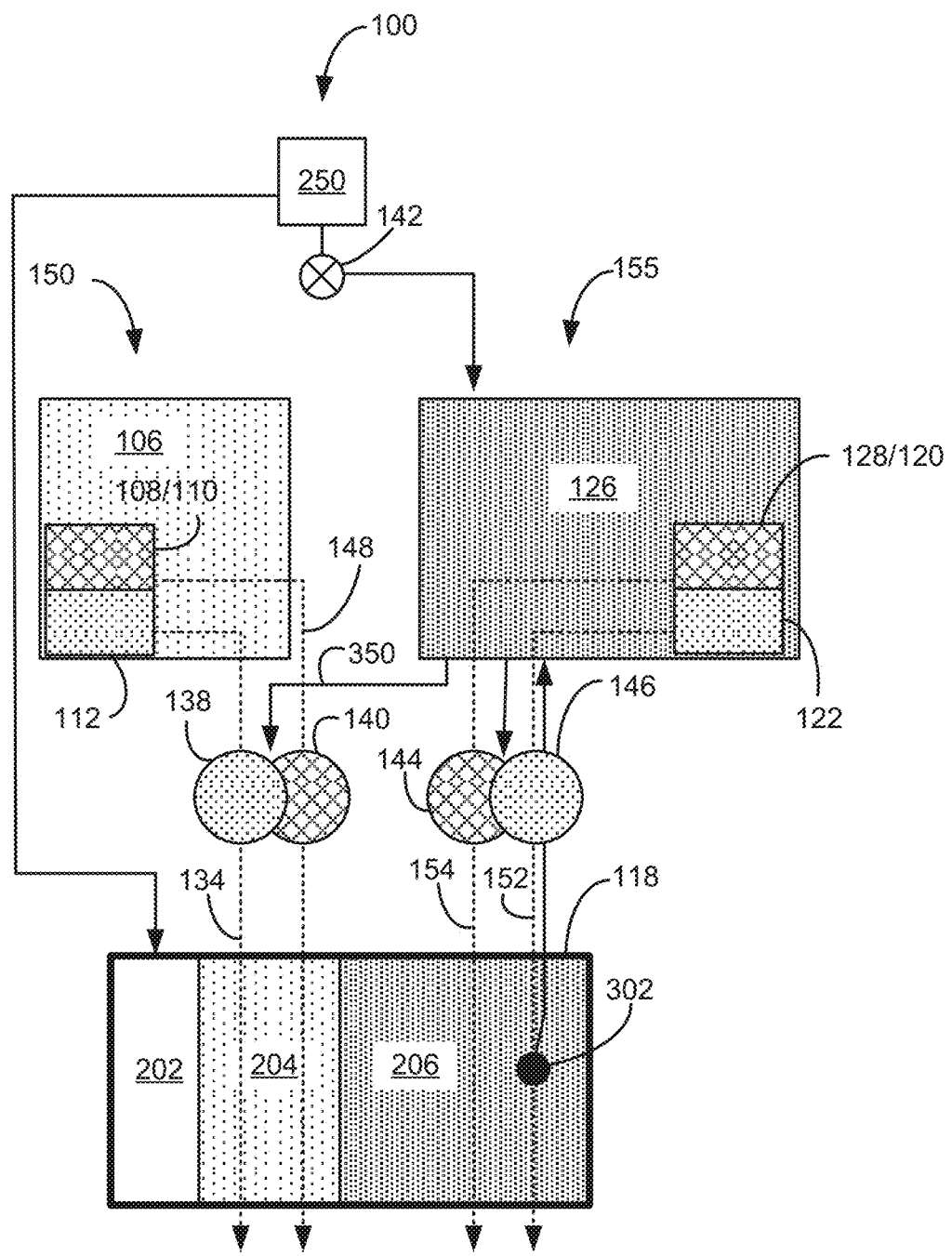
FIGS. 3A, 3B and 3C are simplified block diagrams of a mode of operation of IECS in accordance with some embodiments of the invention.
Figure 3B:
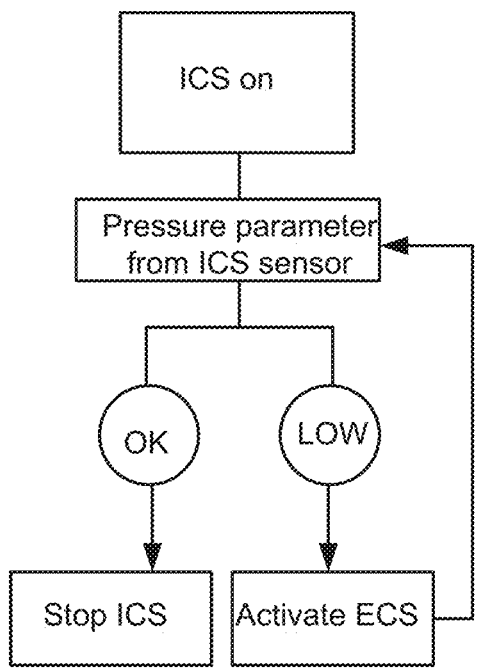
Figure 3C:
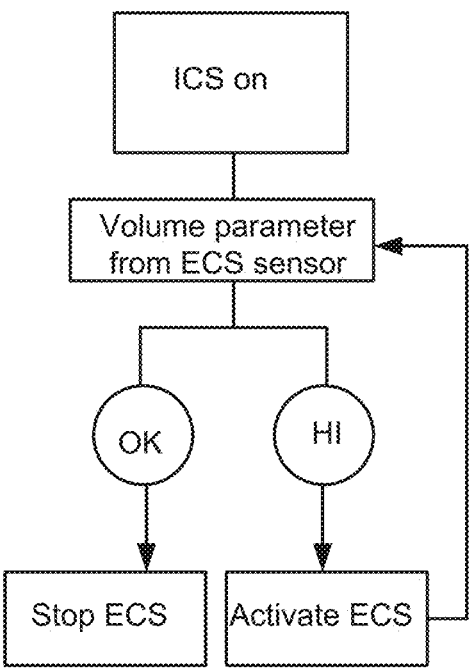

Reference is now made to FIGS. 3A, 3B and 3C, collectively referred to as FIG. 3, which are simplified block diagrams of a mode of operation of IECS 100 in accordance with some embodiments of the invention. As shown in the exemplary embodiment depicted in FIGS. 3A-C, in some embodiments, mode of operation toggle switch 142 is optionally set to operate ICS 155 and ECS 150 in a respectively Master/Slave mode of operation.

In the exemplary configuration depicted in FIGS. 3A-C, ICS 155 is configured to control IWS 155 valves 144/146 as well as EWS 150 valves 138/140 as indicated by an arrow 350. In this configuration ICS 155 is configured to operate independently and automatically activate ECS 150 when needed. For example, in a colonoscopy procedure IECS 100 is introduced into the colon and advanced along the colon up to the cecum. In some embodiments, ICS 155 is activated e.g., to cleanse the colon in preparation for an imaging portion of the procedure. The cleansing process is carried out concurrently with the advancement of IECS 100 in the colon.

In some embodiments, ICS 155 evacuation conduit 152 comprises one or more sensors 302 that communicate operating parameters e.g., lumen pressure and flow of matter in evacuation conduit 152 lumen to IWS 126 processor 124. In some instances, for example, ICS 100 encounters partial or full blockage of evacuation conduit 152 that is reflected by a fall in pressure in the lumen of evacuation conduit 152 sensed by sensor 302 and communicated to IWS 126. IWS 126 is configured to automatically activate ICS 155 based on the received parameters to supplement cleansing operation of ICS 155.

In another example: in some instances during a procedure IECS 100 encounters excessive amounts of matter requiring supplemental suction and evacuation in which case and as depicted in FIGS. 3A-C by an arrow designated reference numeral 350, IWS 155 additionally and optionally is configured to activate EWS 150 one or more valves 138 and/or 140 as needed.

In the exemplary embodiment depicted in FIG. 3B, ICS is activated and receives information regarding operating parameters of the ICS from one or more ICS sensors. In some embodiments, the data is received in a continuous or intermittent manner. In FIG. 3B the operating parameter comprises a pressure parameter indicating e.g., pressure inside ICS evacuation conduit 152. A fall in pressure (a "Low" indication) may indicate partial or complete blockage of the evacuation conduit 152 bringing ICS 155 IWS 126 to activate ECS 150 to evacuate matter e.g., from a colon.

In the exemplary embodiment depicted in FIG. 3C, ICS is activated and receives information regarding operating parameters of the ICS from one or more ICS sensors. In some embodiments, the data is received in a continuous or intermittent manner. In FIG. 3C the operating parameter comprises a matter volume parameter indicating e.g., high volume of matter inside ICS evacuation conduit 152. Hi volume indication (a "HI" indication) may indicate e.g., too high a volume of matter in a colon for ICS 155 evacuation conduit 152 to evacuate alone bringing ICS 155 IWS 126 to activate ECS 150 to evacuate excessive matter from the colon.

Although drawn separately for purposes of presentation in FIG. 3A, it should be understood that in some embodiments, ICS 155 group 206 and ECS 150 group 204 share one or more tubes, for example as described in relation to FIG. 2B, FIG. 9 and/or FIG. 1, herein.

EWS/IWS "Smart" Master/Slave Mode of Operation

Figure 4A:
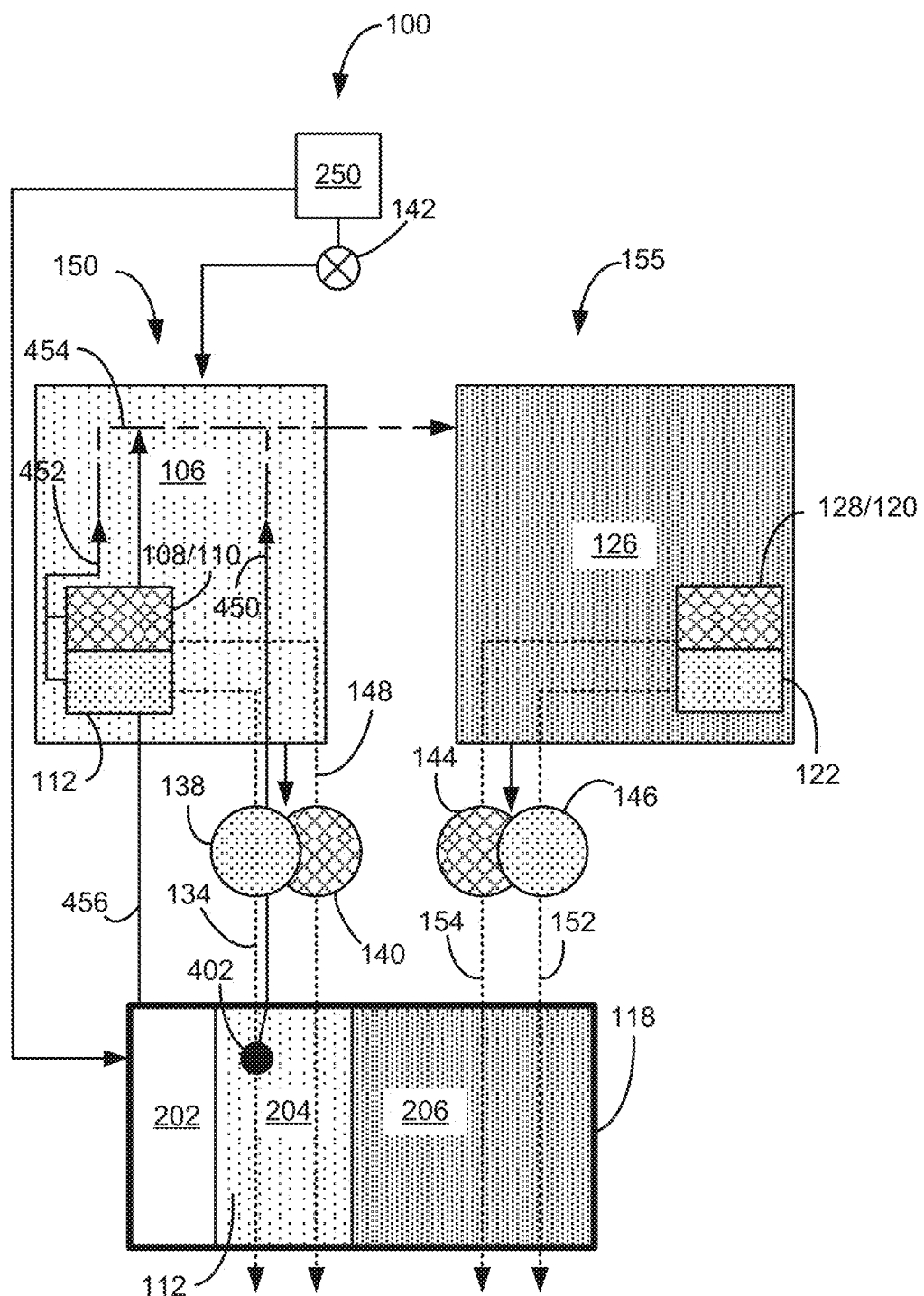
FIGS. 4A, 4B and 4C are simplified block diagrams of a mode of operation of IECS in accordance with some embodiments of the invention.
Figure 4B:
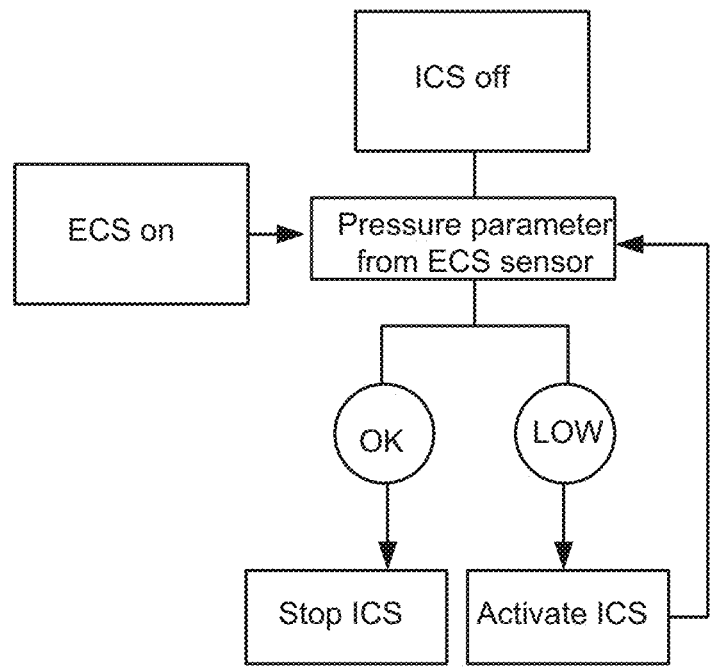
Figure 4C:
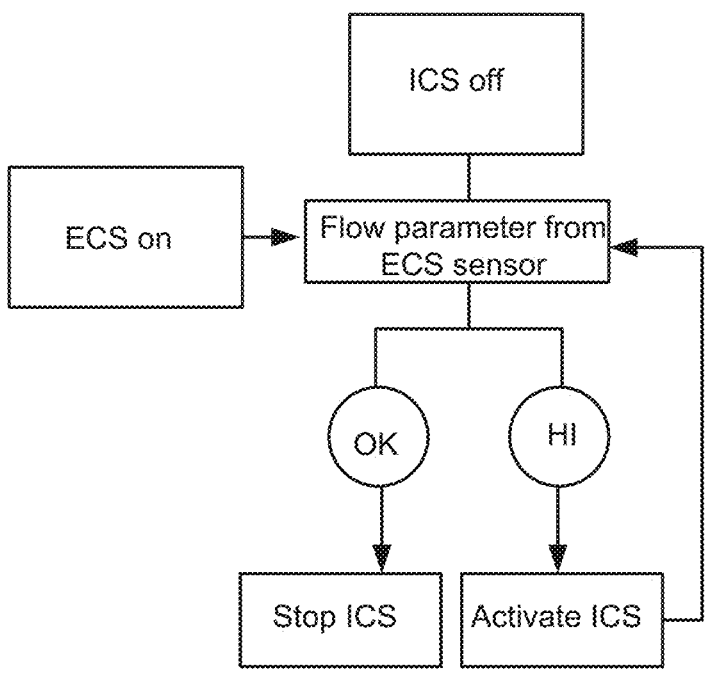

Reference is now made to FIGS. 4A, 4B and 4C collectively referred to as FIG. 4, which are simplified block diagrams of a mode of operation of IECS 100 in accordance with some embodiments of the invention. As shown in the exemplary embodiment depicted in FIGS. 4A-C, in some embodiments, mode of operation toggle switch 142 is optionally set to operate ECS 150 and ICS 155 in a respectively Master/Slave mode of operation. Alternatively and optionally, mode of operation toggle switch 142 is optionally set to operate ICS 155 and ECS 150 in a respectively Master/Slave mode of operation.

In some embodiments, a lumen of at least one of ECS 150 working channel 134 and ICS 155 evacuation conduit 152 comprises one or more sensors disposed in one or more corresponding ECS 150 and ICS 155 components being in data communication with corresponding EWS 106 and IWS 126. In some embodiments, the one or more sensors comprise at least one of a pressure sensor, contact sensor and flowmeter. In the exemplary configuration depicted in FIGS. 4A-C, a sensor 402 is disposed in a lumen of working channel 134 providing EWS 106 processor 114 data regarding working channel 134 operating parameters e.g., lumen pressure and flow of matter in working channel 134 lumen. In some embodiments, sensor 402 is configured to alert EWS 106 processor 114 when lumen of working channel 134 is blocked e.g., by a tool. In some embodiments, the operating parameters include parameters originating from function group 202 e.g., image acquisition data as indicated in FIGS. 4A-C by an arrow 456.

In the configuration depicted in FIGS. 4A-C, ECS 150 is activated and operating parameters described elsewhere herein are communicated e.g., from sensor 402 and/or valves 138/140 to EWS 106 processor 114 as indicated by arrow 450 and from EWS 106 processor 114 to IWS 126 processor 124 indicated by arrow 454. Additionally and optionally, operating parameters, e.g., rate of flow, fluid level, fluid weight and fluid pressure are communicated from ECS 150 components e.g., from EWS 106 air 108 and/or water 110 sources to EWS 106 processor 114 as indicated by arrow 452 and from EWS 106 processor 114 to IWS 126 processor 124 indicated by arrow 454. Additionally and optionally, operating parameters, e.g., image information, are communicated from ECS 150 function group 202 components e.g., camera (not shown) to EWS 106 processor 114 indicated by arrow 456 and from EWS 106 processor 114 to IWS 126 processor 124 indicated by arrow 454.

In the exemplary embodiment shown in FIGS. 4A-C, IWS 126 processor 124 is configured to process the operating parameters received from EWS 106 processor 114 as explained elsewhere herein and automatically activate ICS 155 based on the received parameters. For example and in some embodiments, in a colonoscopy procedure, following introduction and advancement of IECS 100 into the colon, a user 250 employs function group 202 to image the colon as IECS 100 is gradually retracted from the cecum and gradually out of the colon. In some instances, ICS 155 is activated e.g., to cleanse the colon in areas in which a field of view is blocked by colon lumen matter e.g., fecal matter.

In some instances the ability of ECS cleaning operation is insufficient and requires supplementary cleaning and/or agitation and break up of matter in the imaged lumen. In some embodiments, IWS 126 receives operating parameters, e.g., image information, communicated from ECS 150 function group 202 components e.g., camera (not shown) via EWS 106 processor 114. IWS 126 is configured to automatically activate ICS 155 based on the received operating parameters e.g., image information to supplement cleansing operation of ECS 150. Once parameters return to acceptable levels e.g., clear received image, indicating that supplemental cleansing is no longer needed, IWS 126 is configured to automatically stop ICS 155 activity based on the received operating parameters.

In another example, in some instances working channel 134 is clogged or blocked by matter suctioned from lumen of a colon. A fall in pressure in a lumen of working channel 134 is sensed by a sensor e.g., sensor 402, and communicated to IWS 126 via EWS 150. IWS 126 is configured to automatically activate ICS 155 based on the received parameters to supplement cleansing operation of ECS 150. Once parameters return to acceptable levels e.g., working channel 134 lumen pressure is normal, indicating that supplemental cleansing is no longer needed, IWS 126 is configured to automatically stop ICS 155 activity based on the received operating parameters.

In the exemplary embodiment depicted in FIG. 4B, ECS 150 is activated and ICS 155 receives information regarding operating parameters of ECS from one or more ECS sensors. In some embodiments, the data is received in a continuous or intermittent manner. In FIG. 4B the operating parameter comprises a pressure parameter indicating e.g., pressure inside ECS working channel 134. A fall in pressure (a "Low" indication) may indicate partial or complete blockage of the working channel 134 bringing ICS 155 IWS 126 to activate ICS 155 to evacuate matter via ICS evacuation conduit 152; e.g., from a colon.

In the exemplary embodiment depicted in FIG. 4C, ECS 150 is activated and ICS 155 receives information regarding operating parameters of ECS 150 from one or more ECS sensors. In some embodiments, the data is received in a continuous or intermittent manner. In FIG. 4C the operating parameter comprises a matter volume parameter indicating, e.g., a high volume of matter inside ECS working channel 134. Hi volume indication (a "HI" indication) may indicate e.g., too high a volume of matter in a colon for ECS 150 working channel 134 to evacuate alone bringing ICS 155 IWS 126 to activate ICS 150 evacuation channel 152 to evacuate excessive matter from the colon.

Although drawn separately for purposes of presentation in FIG. 4A, it should be understood that in some embodiments, ICS 155 group 206 and ECS 150 group 204 share one or more tubes, for example as described in relation to FIG. 2B, FIG. 9 and/or FIG. 1, herein.

EWS/IWS Master/Slave Mode of Operation

Figure 5A:
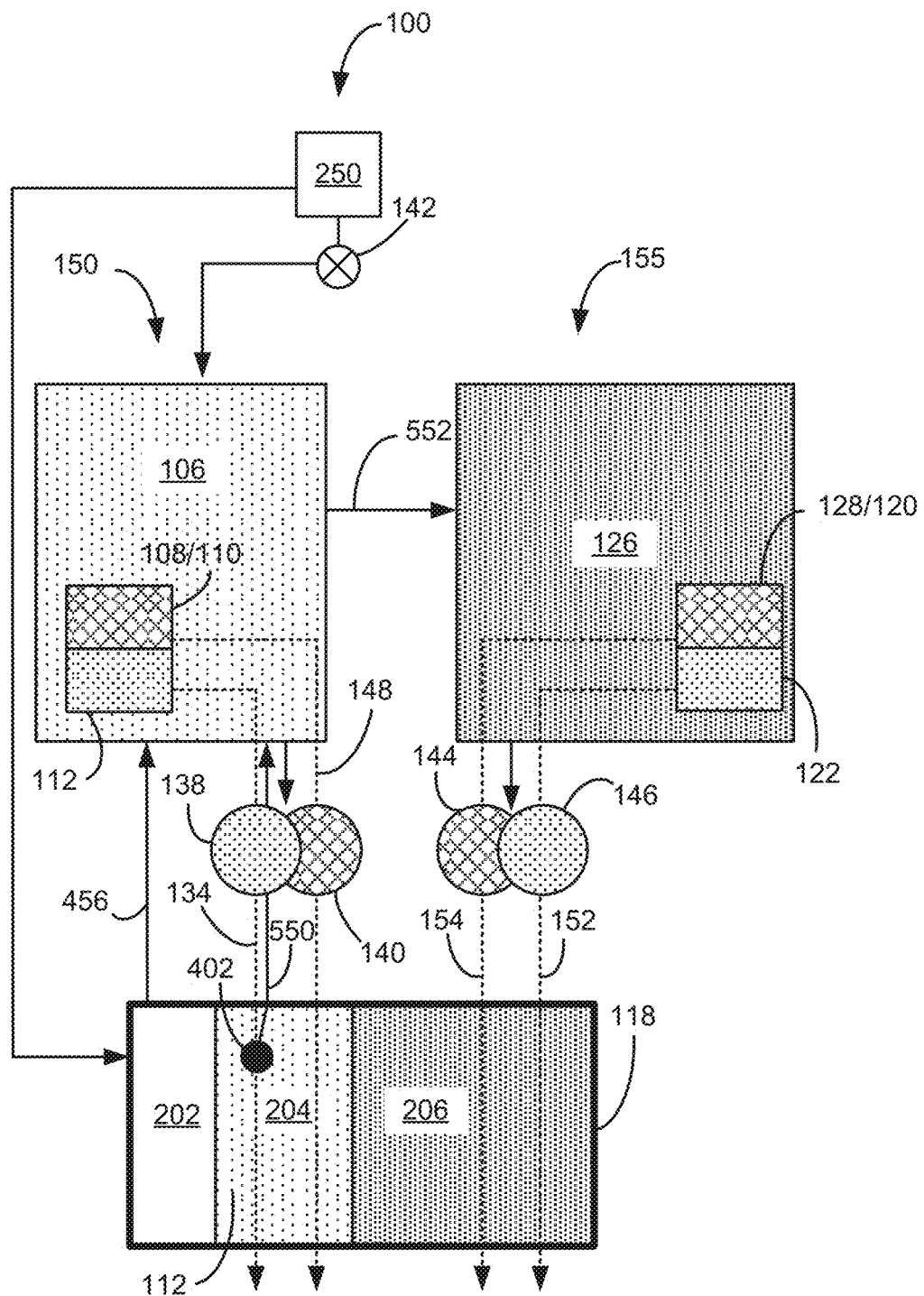
FIGS. 5A, 5B and 5C are simplified block diagrams of a mode of operation of IECS in accordance with some embodiments of the invention.
Figure 5B:
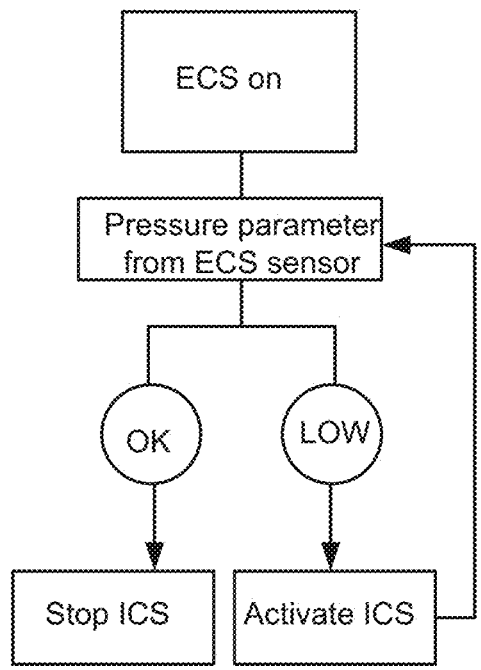
Figure 5C:
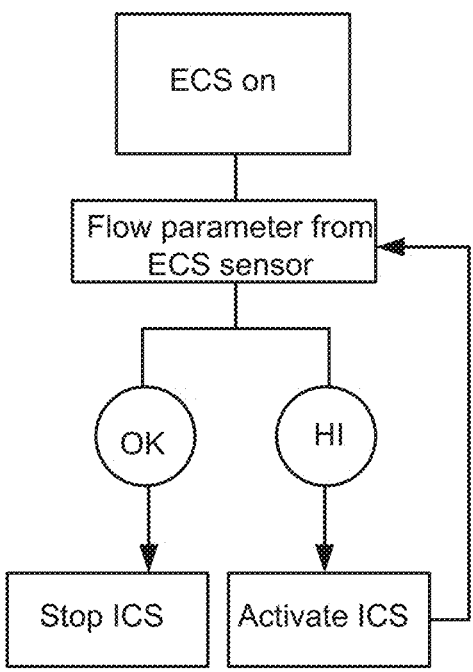

Reference is now made to FIGS. 5A, 5B and 5C collectively referred to as FIG. 5, which are simplified block diagrams of a mode of operation of IECS 100 in accordance with some embodiments of the invention. As shown in the exemplary embodiment depicted in FIGS. 5A-C, in some embodiments, mode of operation toggle switch 142 is optionally set to operate ECS 150 and ICS 155 in a respectively Master/Slave mode of operation. Alternatively and optionally, mode of operation toggle switch 142 is set to operate ICS 155 and ECS 150 in a respectively Master/Slave mode of operation.

In the exemplary configuration depicted in FIGS. 5A-C, one or more sensors 402 comprising at least one of a pressure sensor, contact sensor and flowmeter are disposed in a lumen of working channel 134. In some embodiments, one or more sensors 402 are configured to provide EWS 106 processor 114 with operating parameters regarding working channel 134; e.g., lumen pressure and flow of matter in working channel 134 lumen. In some embodiments, the operating parameters include parameters originating from function group 202; e.g., image acquisition data as indicated in FIGS. 5A-C by an arrow 456.

In the configuration depicted in FIGS. 5A-C, ECS 150 is activated and operating parameters described elsewhere herein are communicated e.g., from sensor 402 and/or valves 138/140 to EWS 106 processor 114 as indicated by arrow 550. Additionally and optionally, operating parameters, e.g., rate of flow, fluid level, fluid weight and fluid pressure are communicated from ECS 150 EWS 106 components e.g., air 108 and/or water 110 sources, to EWS 106 processor 114. Additionally and optionally, operating parameters, e.g., image information, are communicated from ECS 150 function group 202 components e.g., camera (not shown) to EWS 106 processor 114 indicated by arrow 456.

In the exemplary embodiment shown in FIGS. 5A-C, EWS 106 processor 114 is configured to process the received operating parameters and activate ICS 155 based on the received operating parameters. For example and in some embodiments, in a colonoscopy procedure, following introduction and advancement of IECS 100 into the colon, a user 250 employs function group 202 to image the colon as IECS 100 is gradually retracted from the cecum and gradually out of the colon. In some instances, ICS 155 is activated e.g., to cleanse the colon in areas in which a field of view is blocked by colon lumen matter e.g., fecal matter.

In some instances the ability of ECS cleaning operation is insufficient and requires supplementary cleaning and/or agitation and break up of matter in the imaged lumen. In some embodiments, EWS 106 is configured to automatically activate ICS 155 as indicated by arrow 552 based on the received operating parameters to supplement cleansing operation of ECS 150.

In another example, in some instances working channel 134 is clogged or blocked by matter suctioned from lumen of a colon. A fall in pressure in a lumen of working channel 134 is sensed by a sensor e.g., sensor 402, and communicated to EWS 150. As described elsewhere herein, EWS 106 is configured to automatically activate ICS 155 as indicated by arrow 552 based on the received operating parameters to supplement cleansing operation of ECS 150.

In reference to Master/Slave operating modes described herein, at least one of ECS/ICS/EWS/IWS designated as a Master operating system is operative to activate at least one of corresponding ECS/ICS/EWS/IWS designated as a Slave operating system continuously or intermittently and/or inactivate at least one of corresponding ECS/ICS/EWS/IWS designated as a Slave operating system when received operating parameters as described elsewhere herein indicate that operation of a Slave operating system is no longer required.

In the exemplary embodiment depicted in FIG. 5B, ECS 150 is activated and receives information regarding operating parameters of ECS from one or more ECS sensors. In some embodiments, the data is received in a continuous or intermittent manner. In FIG. 5B the operating parameter comprises a pressure parameter indicating e.g., pressure inside ECS working channel 134. A fall in pressure (a "Low" indication) may indicate partial or complete blockage of the working channel 134 bringing ECS 150 EWS 116 to activate ICS 155 to evacuate matter via ICS evacuation conduit 152; e.g., from a colon.

In the exemplary embodiment depicted in FIG. 5C, ECS 150 is activated and receives information regarding operating parameters of ECS 150 from one or more ECS sensors. In some embodiments, the data is received in a continuous or intermittent manner. In FIG. 5C the operating parameter comprises a matter volume parameter indicating, e.g., a high volume of matter inside ECS working channel 134. Hi volume indication (a "HI" indication) may indicate e.g., too high a volume of matter in a colon for ECS 150 working channel 134 to evacuate alone bringing ECS 150 EWS 116 to activate ICS 150 evacuation channel 152 to evacuate excessive matter from the colon.

Figure 6:
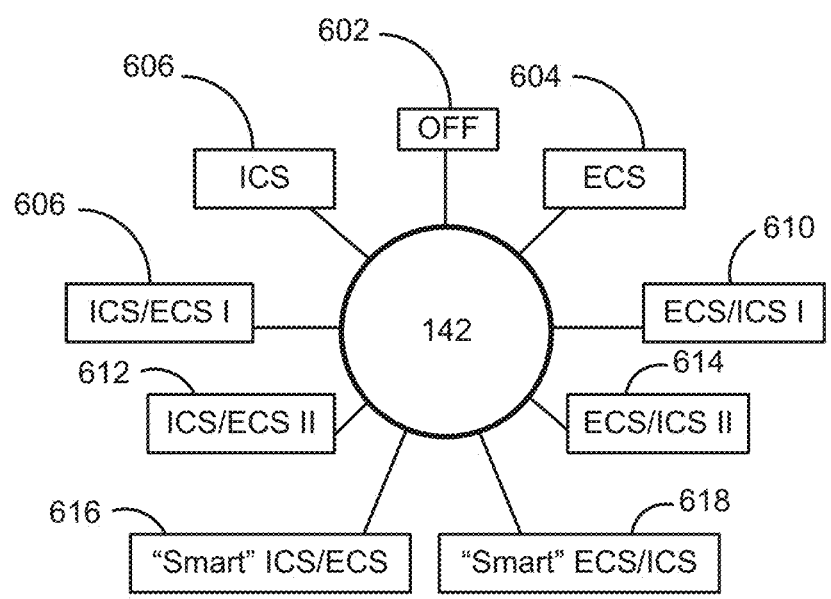
FIG. 6 is a simplified block diagram of an IECS mode of operation toggle switch in accordance with some embodiments of the invention.

Reference is now made to FIG. 6, which is a simplified block diagram of an IECS mode of operation toggle switch in accordance with some embodiments of the invention. In the exemplary embodiment depicted in FIG. 6 toggle switch 142 is configured to select between one or more modes of operation including: (a) Off mode 602 in which IECS 100 is turned off. (b) ECS mode 604—in which only ECS 150 is activated (c) ICS mode 606—in which only ICS 155 is activated. (d) ICS/ECS I Master/Slave mode 608—in which ICS 155 is activated and is configured to automatically optionally continuously or intermittently activate ECS 150 valves 138/140 as explained elsewhere herein. (e) ECS/ICS I Master/Slave mode 610—in which ECS 150 is activated and is configured to automatically optionally continuously or intermittently activate ICS 155 valves 144/146 as explained elsewhere herein. (f) ICS/ECS II Master/Slave mode 612—in which ICS 155 is activated and is configured to automatically optionally continuously or intermittently activate ECS 150. (g) ECS/ICS II Master/Slave mode 614—in which ECS 150 is activated and is configured to automatically optionally continuously or intermittently activate ICS 155. (h) "Smart" ICS/ECS Master/Slave mode 616—in which ICS 155 is activated and automatically optionally continuously or intermittently ECS 150 is activated by processor 114 based on received operating parameters from ICS 155 as explained elsewhere herein. (i) "Smart" ECS/ICS Master/Slave mode 618—in which ECS 150 is activated and automatically optionally continuously or intermittently ICS 155 is activated by processor 124 based on received operating parameters from ECS 150 as explained elsewhere herein.

Although drawn separately for purposes of presentation in FIG. 5A, it should be understood that in some embodiments, ICS 155 group 206 and ECS 150 group 204 share one or more tubes, for example as described in relation to FIG. 2B, FIG. 9 and/or FIG. 1, herein.

Figure 7A:
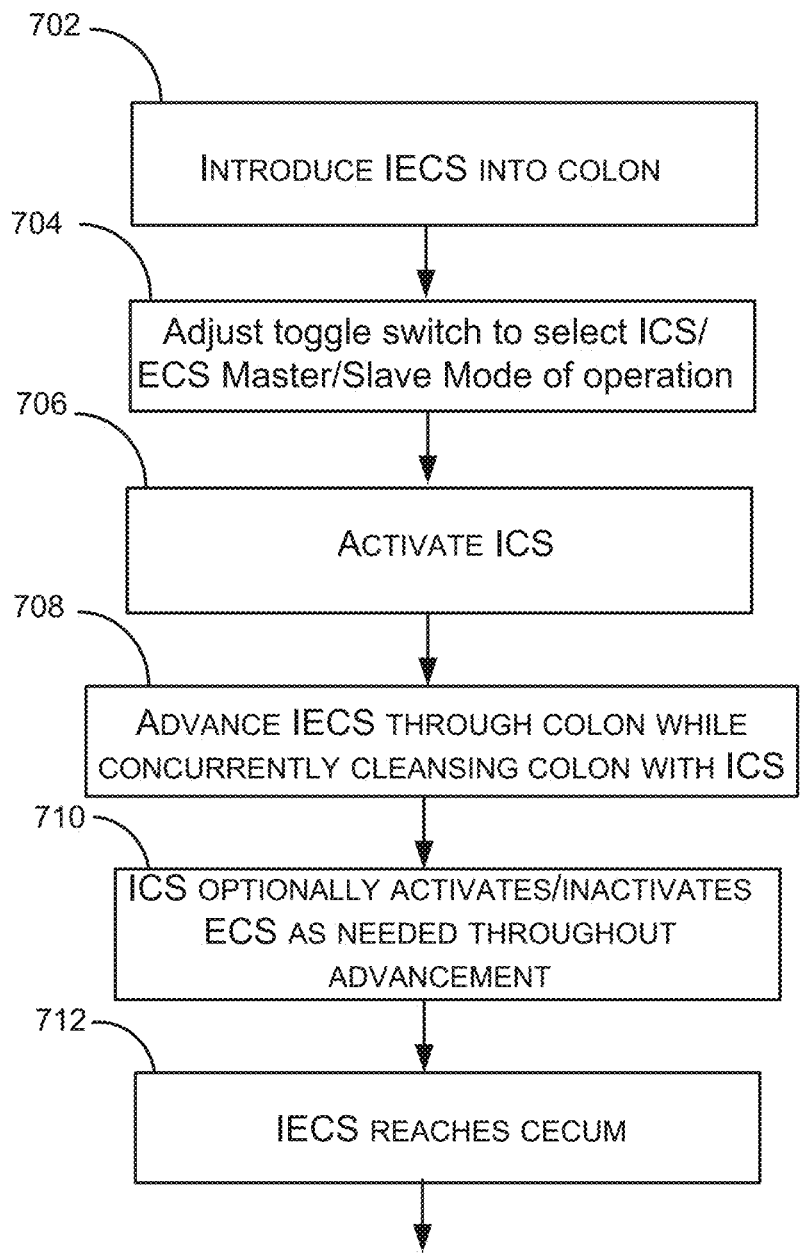
FIGS. 7A and 7B are a simplified flow chart of implementation of IECS in a colonoscopy procedure in accordance with some embodiments of the invention.
Figure 7B:
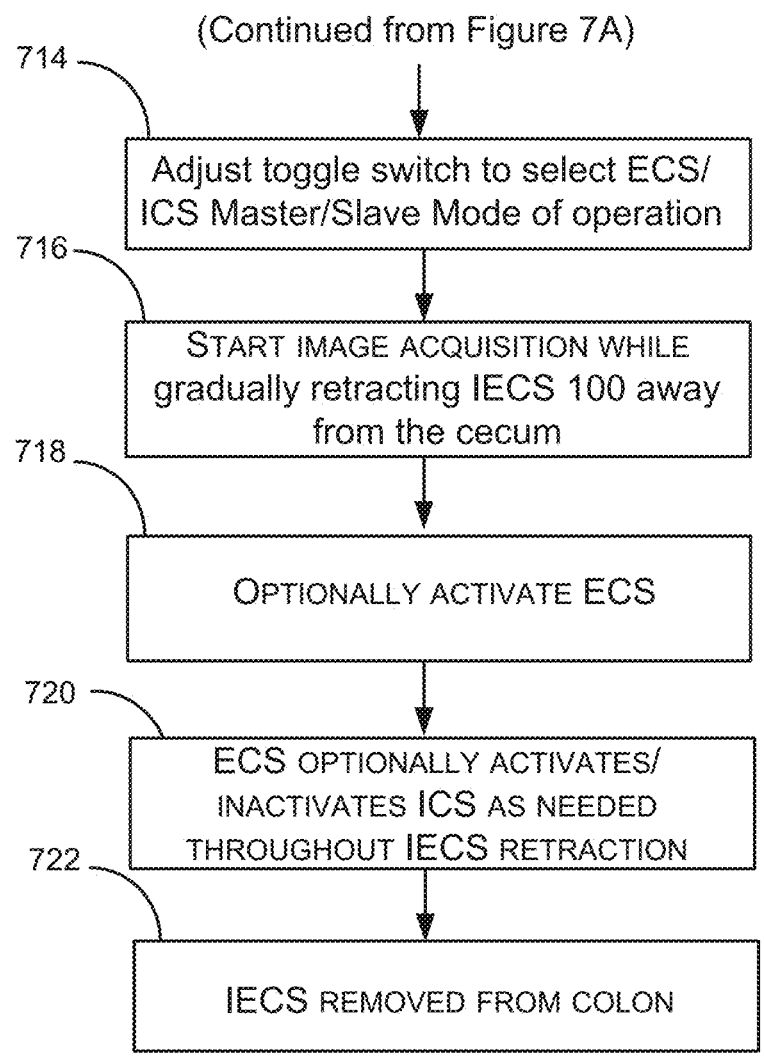

Reference is now made to FIGS. 7A and 7B; which are a simplified flow chart of implementation of IECS 100 in a colonoscopy procedure in accordance with some embodiments of the invention. A colonoscopy procedure commonly requires preparation to cleanse out the content of the colon and to allow proper imaging of the colon wall. However, in some instances, preparation is incomplete, insufficient or has not been done at all. In such circumstances a colonoscopy comprises at least two phases: a cleansing phase that is carried out concurrently with the introduction of the colonoscope into the colon and an imaging phase that follows the cleansing phase and is commonly carried out during the colonoscope withdrawal from the colon.

As explained in greater detail elsewhere herein, IECS 100 comprises an ICS 155 configured to agitate and break down colon lumen fecal matter so to enable effective evacuation of the matter out of the colon.

In some embodiments and as described elsewhere herein, an exemplary and optional method of implementing IECS 100 in a colonoscopy procedure comprises at 702 introducing IECS 100 into a colon and adjusting at 704 IECS mode of operation toggle switch 142 to ICS/ECS Master/Slave mode of operation 606/612 and activating ICS 155 at 706. The method further comprises at 708 guiding IECS 100 through the colon while concurrently cleansing the colon with ICS 155. At 710 optionally activating or inactivating ECS 150 optionally automatically as needed throughout the advancement of IECS 100 to supplement the cleansing operation of ICS 155 and reaching the cecum at 712. This completes the cleansing phase of the colon at which time the imaging phase of the method begins at 714 in adjusting IECS mode of operation toggle switch 142 to ECS/ICS Master/Slave mode of operation 610/614 and at 716 starting image acquisition while gradually retracting IECS 100 in the colon away from the cecum. Optionally, at 718, activating ECS 150 and optionally at 720 activating or inactivating ICS 155 optionally automatically as needed throughout the retraction of IECS 100 along and out of the colon to supplement the cleansing operation of ECS 150 until fully removing IECS 100 from the colon at 722.

IECS Interface Portion

Figure 8A:
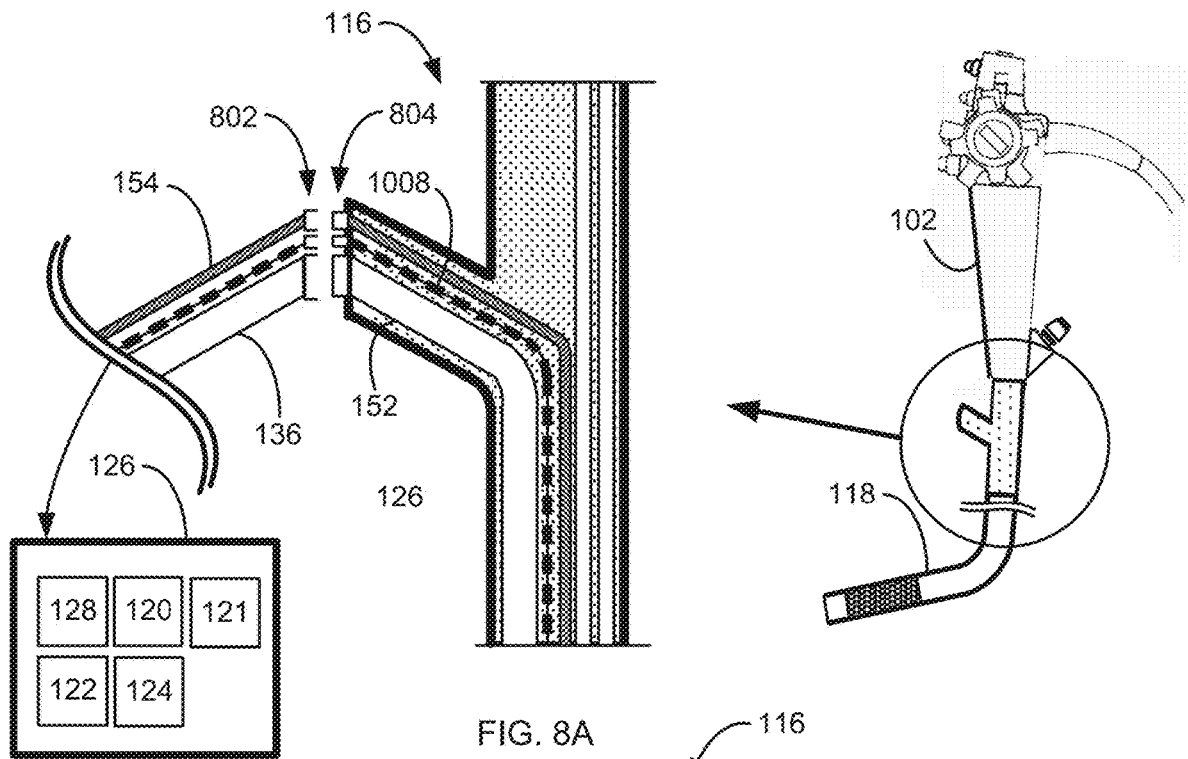
FIGS. 8A and 8B are part block diagram, cross-section view, simplified illustrations of an IECS interface in accordance with some embodiments of the invention.
Figure 8B:
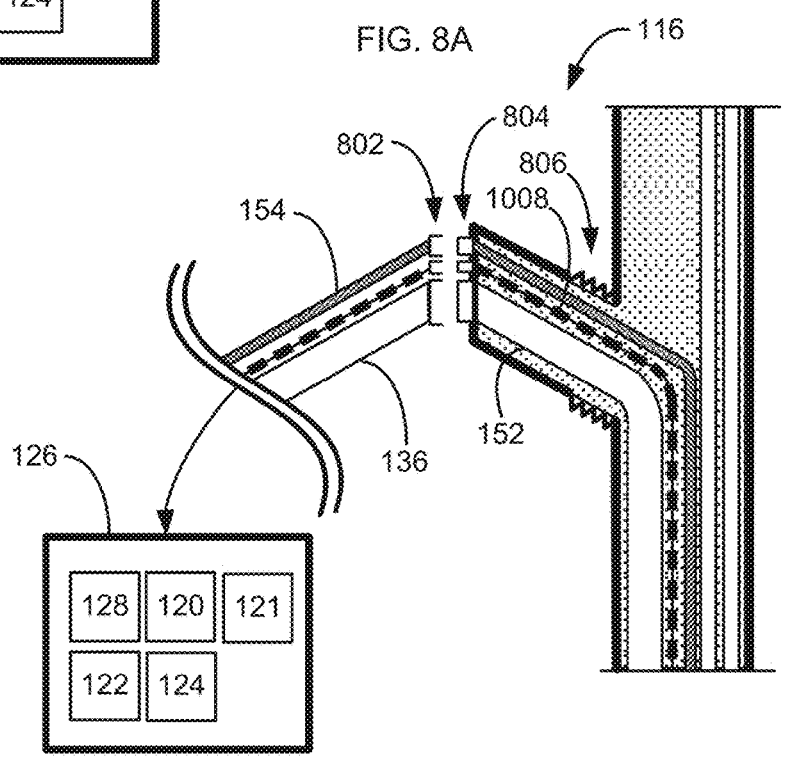

Reference is now made to FIGS. 8A and 8B, which are part block diagram, cross-section view, simplified illustrations of an IECS interface in accordance with some embodiments of the invention. As shown in FIG. 8A and described in detail elsewhere herein, IECS 100 comprises at least three function groups: Endoscope operating function group 202, ECS 150 function group 204 and ICS 155 function group 206.

In some embodiments, and as shown in the exemplary embodiment depicted in FIG. 8A, ICS 155 function group 206 including one or more irrigation fluid supply tubes 154; e.g., air and/or water supply tubes, coupled to air 128 and/or water 120 sources, one or more evacuation conduits 152 in fluid communication with vacuum source 122 and optionally a sensor (e.g., sensor 302) associated circuitry 1008 in communication with IWS 126 processor 124 enter IECS 100 insertion tube 118 via IECS interface 116 via at least one umbilical cable 136 between ICS Working Station (IWS) 126 and IECS 100 interface 116.

Umbilical cable 136 terminates at the IECS 100 end at a quick release coupling 802 configured to couple to an entry port 804 of interface 116. In some embodiments, umbilical cable 136 is disposable.

Optionally, in some embodiments and as shown in FIG. 8B, interface 116 comprises a flexible joint 806 configured to allow flexion and extension of interface 116 branch 808 and increase comfort of coupling interface 116 and umbilical cable 136.

Insertion Tube Components

Reference is now made to FIG. 9, which is a cross-section view simplified illustration of IECS insertion tube in accordance with some embodiments of the invention.

In some embodiments, and as shown in the exemplary embodiment depicted in FIG. 9, in which a cross-section of insertion tube 118 is taken along section A-A, insertion tube 118 comprises endoscope operating function group 202 comprising at least one or more endoscope navigation cables 902, light bundle 1004 and image acquisition camera cable 906.

Additionally and optionally, in some embodiments, insertion tube 118 comprises endoscope operating function group 204 comprising at least one or more suction/working channels 134 and one or more irrigation and/or air 178/water 170 supply tubes coupled to air 108 and/or water 110 sources.

As shown in the exemplary embodiment depicted in FIG. 9, insertion tube 118 comprises ICS 155 function group 206 including one or more irrigation or fluid supply tubes 154; e.g., air and/or water supply tubes, one or more evacuation conduits 152 in fluid communication with vacuum source 122 and optionally a sensor (e.g., sensor 302) and sensor 302 associated circuitry 908.

In some embodiments, ICS 155 function group 206 and endoscope operating function group 204 are configured to at least partially overlap in the tubes belonging to each, and share control of evacuation and/or fluid supply. In some embodiments, evacuation tube 152 joins to (and optionally comprises or is identical to) working channel 134, with one or both of working channel 134 and evacuation tube 152 being joined (e.g., by means of a Y-tube connection) to both the EWS 106 (e.g., via control valve 138) and to the IWS 126 (e.g., via control valve 146). Additionally or alternatively, in some embodiments, fluid supply tube 154 joins to (and optionally comprises or is identical to) fluid supply tube 148, with one or both of fluid supply tube 148 and fluid supply tube 154 being joined (e.g., by means of a Y-tube connection) to the EWS 106 (e.g., via control valve 140) and to the IWS 126 (e.g., via control valve 144).

In some embodiments, a diameter of insertion tube 118 is between 17 and 22 mm, between 18 and 20 mm, less than 17 mm, more than 22 mm or any diameter in between. In some embodiments, a diameter of insertion tube 118 is equal to 19 mm. In some embodiments, a diameter of insertion tube 118 is less than 19 mm. In some embodiments, one or more evacuation conduits 152 comprises a diameter in the range between 2 and 10 mm, 4 and 8 mm or 5-6 mm, less than 2 mm or more than 10 mm and any diameter in between. In some embodiments, the diameter of evacuation conduits 152 is between 5.4 mm and 6.0 mm. In FIG. 9, the components of insertion tube 118 are depicted distanced from one another for clarity of explanation. In some embodiments, the components of insertion tube 118 are positioned in close proximity to reduce the diameter of insertion tube 118 as much as possible e.g., less than 20 mm.

Figure 10:
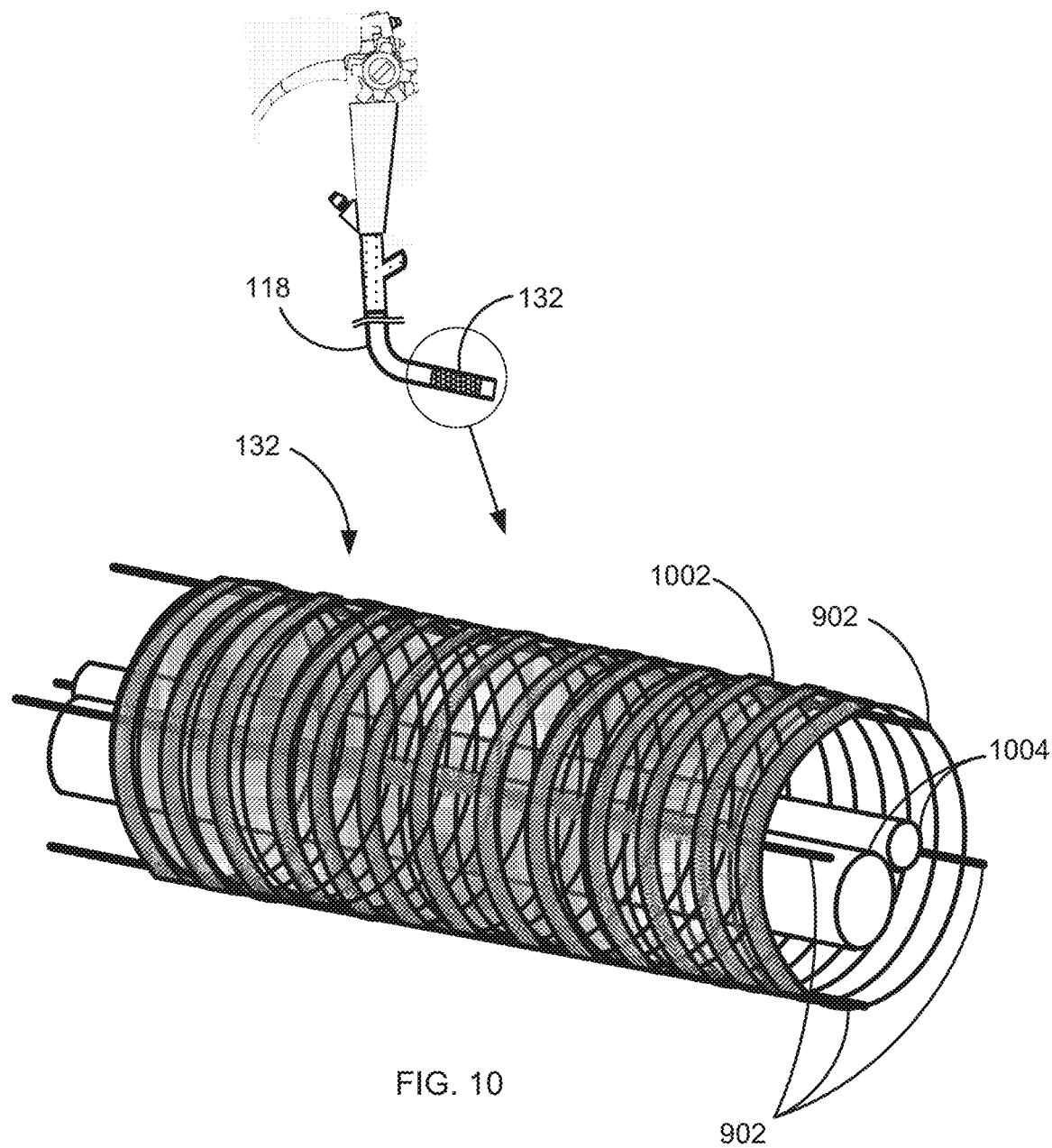
FIG. 10 is a perspective view simplified illustration of an IECS endoscope insertion tube bendable portion in accordance with some embodiments of the invention.

As shown in FIG. 10, which is a perspective view simplified illustration of endoscope insertion tube 118 bendable portion 132 in accordance with some embodiments of the invention, in some embodiments, bendable portion 132 is configured to be driven by one or more endoscope navigation cables 902 and bend radially at least up to 180 degrees in vertical (up and down) directions and at least up to 160 degrees in horizontal (left and right) directions to aim distal end tip 130 in a desired direction.

In some embodiments, bendable portion 132 comprises a braided or ribbed wall 1002 made of a resilient material e.g., rubber. In some embodiments, bendable portion 132 comprises a spiral form wall.

In some embodiments, all tubes housed within insertion tube 118 and bendable portion 132 represented in FIG. 10 by tubes 1004 are made of resilient materials and are bendable in accordance with the bending of bendable portion 132.

Figure 11:
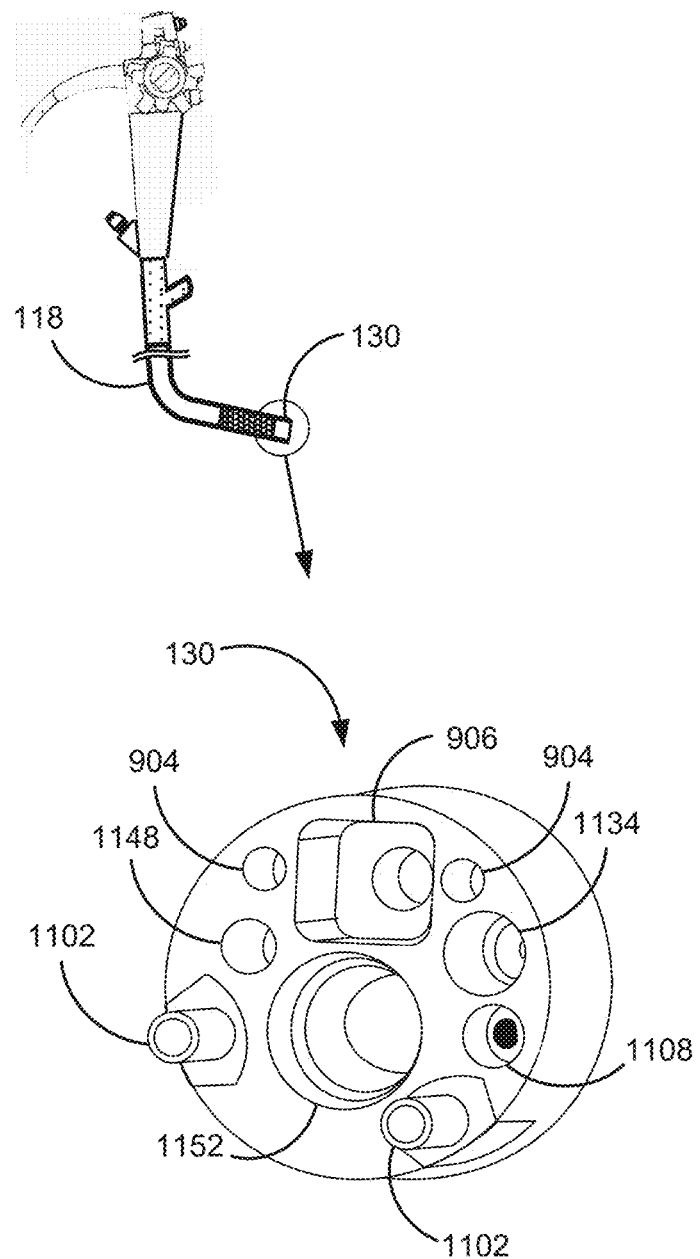
FIG. 11 is a perspective view simplified illustration of an IECS distal tip in accordance with some embodiments of the current invention.

FIG. 11 is a perspective view simplified illustration of an IECS distal tip 130 in accordance with some embodiments of the current invention, viewed from aspect of the back surface depicting attachment ports of bendable portion 132 components. As shown in FIG. 11, an IECS distal tip 130 is configured to attach to a distal tip of bendable portion 132 and comprises one or more light bundle 904 receiving ports 1104, one or more camera receiving ports 906, one or more working channels 134 receiving port 1134, one or more ports 1148 for receiving fluid supply tubes 148 comprising air 178 and/or water 170 supply tubes, one or more evacuation tubes 152 receiving port 1152, one or more sensor 302 circuitry 908 receiving port 1108 and one or more air 128 and/or water 120 supply/irrigation tubes receiving ports and/or fluid jet nozzles 1102.

General

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

As used herein the term "method" refers to manners, means, techniques and procedures for accomplishing a given task including, but not limited to, those manners, means, techniques and procedures either known to, or readily developed from known manners, means, techniques and procedures by practitioners of the medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

In addition, any priority document(s) of this application is/are hereby incorporated herein by reference in its/their entirety.

What is claimed is:

1. An integrated endoscope cleansing system (IECS) comprising:
    an endoscope having:
        at least one insertion tube in communication with an endoscope working station (EWS), and
        at least one working channel functionally coupled to at least one endoscope cleaning system (ECS) vacuum source,
    wherein the EWS is configured to control the ECS vacuum source; and
    an independent cleansing system (ICS) having:
        an independent cleansing system working station (IWS), and
        having at least one ICS evacuation conduit located within at least the insertion tube and functionally coupled to an ICS vacuum source;
    wherein the IWS is configured to control the ICS vacuum source;
    wherein said IECS comprises at least one mode of operation consisting of at least one of:
    (a) ICS/ECS Master/Slave mode of operation;
    (b) ICS/ECS Smart Master/Slave mode of operation; and
    (c) ECS/ICS Master/Slave mode of operation.

2. The system according to claim 1, wherein the at least one ICS evacuation conduit and the at least one working channel together comprise a single channel within the at least one insertion tube.

3. The system according to claim 1, wherein the at least one ICS evacuation conduit and the at least one working channel together comprise a single tube within the at least one insertion tube to which both the ICS vacuum source and the ECS vacuum source are functionally coupled.

4. The system according to claim 1, wherein said IECS comprises at least one mode of operation toggle switch configured to toggle between at least two of said modes of operation.

5. The system according to claim 4, comprising a manual mode of operation, also selected by said toggle, wherein said IECS is configured for manual activation of at least one of said ECS and ICS.

6. The system according to claim 5, wherein said IECS, in the manual mode of operation, is configured to manually activate each of said ECS and ICS individually, sequentially or concurrently.

7. The system according to claim 1, including the ICS/ECS Master/Slave mode of operation; and wherein, in said ICS/ECS Master/Slave mode of operation, the ICS is activated and configured to automatically activate the ECS.

8. The system according to claim 1, wherein at least one of said IWS and EWS comprises at least one processor and at least one sensor configured to communicate at least one operating parameter to said at least one processor.

9. The system according to claim 8, wherein said at least one operating parameter comprises at least one of lumen pressure and flow of matter in a lumen of at least one of said working channel and evacuation conduit.

10. The system according to claim 8, including the ICS/ECS "Smart" Master/Slave mode of operation; and wherein, in the ICS/ECS "Smart" Master/Slave mode of operation, the IWS processor is configured to receive and process said at least one operating parameter received from said EWS processor and automatically activate said ECS based on said received at least one operating parameter.

11. The system according to claim 8, including the ECS/ICS Master/Slave mode of operation; and wherein, in the ECS/ICS Master/Slave mode of operation, the EWS processor is configured to receive and process said at least one operating parameter from said sensor and to automatically activate said ICS based on said received parameter.

12. The system according to claim 1, wherein said endoscope comprises a colonoscope.

13. The system according to claim 1 wherein said insertion tube is configured to receive IECS components associated with at least one operating function group, the at least one operating function comprising at least one of:
    (a) an endoscope operating function group;
    (b) an ECS operating function group; and
    (c) an ICS operating function group.

14. The system according to claim 13, wherein:
    said endoscope operating function group (a) comprises at least one of: an endoscope angulation control navigation cable, light wiring and circuitry, power circuitry, image acquisition camera and circuitry, and sensors and associated circuitry;
    said ECS operating function group (b) comprises at least one suction/working channel and at least one irrigation and/or air/water supply tube;
    wherein said ICS operating function group (c) comprises at least one irrigation and/or air/water supply tube and at least one evacuation conduit.

15. The system according to claim 1, wherein said IECS comprises an interface configured to couple an umbilical cable originating from said IWS to said insertion tube.

16. The system according to claim 15, wherein said umbilical cable comprises: at least one irrigation tube, at least one evacuation conduit, and sensor circuitry.

17. The system according to claim 1, wherein said insertion tube comprises at least one bendable portion.

18. The system according to claim 17, wherein the at least one ICS evacuation conduit located within the insertion tube and housed within said bendable portion is bendable in accordance with the bending of said bendable portion.

19. A method for a colonoscopy procedure, comprising providing an integrated endoscope cleansing system (IECS) comprising:
  an endoscope having:
    at least one mode of operation toggle switch and at least one insertion tube in communication with an endoscope working station (EWS), and
    at least one working channel functionally coupled to at least one endoscope cleaning system (ECS) vacuum source,
  wherein the EWS configured to control the ECS vacuum source; and
  an independent cleansing system (ICS) having:
    an independent cleansing system working station (IWS), and
    at least one ICS evacuation conduit located within at least the insertion tube and functionally coupled to an ICS vacuum source,
  wherein the IWS configured to control the ICS vacuum source;
  introducing the IECS insertion tube into a colon; and
  adjusting the mode of operation toggle switch between a first and a second mode of operation while the IECS insertion tube is within the colon, wherein the first and second modes differ in configuration of a source of control of at least one of the ICS and ECS vacuum sources.

20. The method according to claim 19, wherein said first and second modes of operations are selected from among the group consisting of:
  (a) a manual mode of operation;
  (b) ICS/ECS Master/Slave mode of operation;
  (c) ICS/ECS "Smart" Master/Slave mode of operation; and
  (d) ECS/ICS Master/Slave mode of operation.

21. The method for a colonoscopy procedure according to claim 20, wherein adjusting said mode of operation toggle switch comprises selecting said ICS/ECS Master/Slave mode of operation.

22. The method according to claim 21, further comprising:
  activating said ICS;
  advancing said IECS through said colon up to a cecum while concurrently cleansing said colon with said ICS; and
  automatically activating said ECS by said ICS when needed throughout said advancement.

23. An integrated endoscope cleansing system (IECS) comprising:
  an endoscope having:
    at least one insertion tube in communication with an endoscope working station (EWS), and
    at least one working channel functionally coupled to at least one endoscope cleaning system (ECS) vacuum source,
  wherein the EWS is configured to control the ECS vacuum source; and
  an independent cleansing system (ICS) having:
    an independent cleansing system working station (IWS), and
    having at least one ICS evacuation conduit located within at least the insertion tube and functionally coupled to an ICS vacuum source;
  wherein the IWS is configured to control the ICS vacuum source;
  wherein said IECS comprises an interface configured to couple an umbilical cable originating from said IWS to said insertion tube; said umbilical cable comprising: at least one irrigation tube, at least one evacuation conduit, and a sensing module in communication with the IWS.

* * * * *